US007880876B2

(12) United States Patent
Zhao et al.

(10) Patent No.: US 7,880,876 B2
(45) Date of Patent: *Feb. 1, 2011

(54) METHODS OF USE FOR SURFACE ENHANCED RAMAN SPECTROSCOPY (SERS) SYSTEMS FOR THE DETECTION OF BACTERIA

(75) Inventors: Yiping Zhao, Statham, GA (US); Richard A. Dluhy, Athens, GA (US); Ralph A. Tripp, Watkinsville, GA (US); Yao-wen Huang, Athens, GA (US); Hsiao Yun Chu, Athens, GA (US); Yongjun Liu, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 224 days.

This patent is subject to a terminal disclaimer.

(21) Appl. No.: 12/166,485

(22) Filed: Jul. 2, 2008

(65) Prior Publication Data

US 2009/0303472 A1 Dec. 10, 2009

Related U.S. Application Data

(63) Continuation-in-part of application No. 11/376,661, filed on Mar. 15, 2006, now Pat. No. 7,738,096, which is a continuation-in-part of application No. 11/256,395, filed on Oct. 21, 2005, now Pat. No. 7,658,991, said application No. 11/376,661 application No. 12/166,485, is a continuation-in-part of application No. 11/495,980, filed on Jul. 28, 2006, now Pat. No. 7,583,379, and a continuation-in-part of application No. 11/256,395, filed on Oct. 21, 2005, now Pat. No. 7,658,991, said application No. 11/495,980 is a continuation-in-part of application No. 11/376,661, filed on Mar. 15, 2006, now Pat. No. 7,738,096, application No. 12/166,485.

(60) Provisional application No. 60/620,810, filed on Oct. 21, 2004, provisional application No. 60/662,089, filed on Mar. 15, 2005, provisional application No. 60/703,110, filed on Jul. 28, 2005, provisional application No. 60/662,089, filed on Mar. 15, 2005, provisional application No. 60/947,519, filed on Jul. 2, 2007.

(51) Int. Cl.
*G01J 3/44* (2006.01)

(52) U.S. Cl. .................... 356/301; 436/164; 436/171; 435/6

(58) Field of Classification Search .............. 356/301; 436/164, 171; 435/6
See application file for complete search history.

(56) References Cited

U.S. PATENT DOCUMENTS 6,180,415 B1 1/2001 Schultz et al. ............. 436/518

(Continued)

FOREIGN PATENT DOCUMENTS

EP 0 261 642 9/1987

(Continued)

OTHER PUBLICATIONS

Huang, et al.; Single-Domain Antibody-Conjugated nanoaggregate-Embedded Beads for Targeted Detection of Pathogenic Bacteria; Chem. Eur. J. 2009, 00, 0-0; pp. 1-6.

(Continued)

*Primary Examiner*—L. G Lauchman
(74) *Attorney, Agent, or Firm*—Thomas, Kayden, Horstemeyer & Risley, LLP

(57) ABSTRACT

Surface-enhanced Raman spectroscopic (SERS) systems and methods for detecting biomolecules of interest, such as a bacterium are provided.

18 Claims, 24 Drawing Sheets

U.S. PATENT DOCUMENTS

| | | | |
|---|---|---|---|
| 6,376,177 | B1 | 4/2002 | Poponin .................. 435/6 |
| 7,192,703 | B2 | 3/2007 | Sun et al. |
| 7,267,948 | B2 | 9/2007 | Vo-Dinh |
| 7,361,313 | B2 | 4/2008 | Chan et al. |
| 7,397,558 | B2 | 7/2008 | Kamins et al. |
| 7,400,395 | B2 | 7/2008 | Chan et al. |
| 2004/0224321 | A1 | 11/2004 | Nicolau et al. |
| 2006/0147927 | A1 | 7/2006 | Geddes et al. |
| 2008/0059135 | A1 | 3/2008 | Murugkar et al. |
| 2008/0096005 | A1* | 4/2008 | Premasiri .................. 428/323 |

FOREIGN PATENT DOCUMENTS

| | | |
|---|---|---|
| WO | 2004059279 | 7/2004 |
| WO | 2004074790 | 9/2004 |
| WO | WO 2006/005111 | 7/2005 |
| WO | WO 2006/066180 | 6/2006 |
| WO | 2006/137885 | 12/2006 |
| WO | 2007059514 | 5/2007 |
| WO | 2008045114 | 4/2008 |

OTHER PUBLICATIONS

Bentley; "Microsensors: Invisible Watchdogs to Keep Us Safe and Well"; http://www.solve.csiro.au/0805/article1.htm; Aug. 2005; 4 pages.

Campion, et al.; "Surface-enhanced Raman scattering"; Chemical Society Reviews, vol. 27; 1998; 10 pages.

Carillo; "Sers nanoparticles: a new optical detection modality for rapid tests"; http://www.cli-online.com/en/featured-articles/sers-nanoparticles-a-new-optical-detection-modality-for-rapid-tests/trackback/1/index.html; Copyright 2004-2007; 4 pages.

Clin; "Applications of Nanobiotechnology in Clinical Diagnostics"; http://www.clinchem.org/cgi/content/full/53/11/2002; 2007; 1 page.

Driskell, et al.; "Low-Level Detection of Viral Pathogens by a Surface-Enhanced Raman Scattering Based Immunoassay"; 2005; 8 pages.

Fischer, et al.; "Heightened sense for sensing: recent advances in pathogen immunoassay sensing platforms"; Lawrence Livermore National Laboratory; Feb. 6, 2007; 13 pages.

Goeller, et al.; "Discrimination of Bacteria and Bacteriophages by Raman Spectroscopy and Surface-Enhanced Raman Spectroscopy"; Society for Applied Spectroscopy; vol. 61; Nov. 7, 2007; 7 page.

Gordon, et al.; "Plasmonic Sensors Based on Nano-Holes: Technology and Integration"; Micro and Nanotechnologies for Space, Defense, and Security II; vol. 6959; 2008; 6 pages.

Grabar, et al.; "Preparation and Characterization of Au Colloid Monolayers"; The Pennsylvania State University; vol. 67 Feb. 15, 1995; 9 pages.

Grow, et al.; "Evaluation of the Doodlebug: A Biochip for Detecting Waterborne Pathogens"; http://www.iwapublishing.conn/template.cfm?name=isbn1843396688; Jun. 1, 2003; 1 page.

Grow, et al.; "New biochip technology for label-free detection of pahogens and their toxins"; Biopraxis, Inc.; Journal of Microbiological Methods; 2003; 13 pages.

Gu, et al.; "Biofunctional magnetic nanoparticles for protein separation and pathogen detection"; ChemComm; Jan. 19, 2006; 9 pages.

Hou, et al.; "Rapid Chip-Scale Detection by Micro-Spiral Flow and Surface Enhanced Raman Scattering"; http://aiche.confex.com/aiche/2006/techprogram/P66060.HTM; Nov. 15, 2006; 2 pages.

Kao, et al.; "Surface-Enhanced Raman Detection on Metalized Nanostructured Poly(p-xylylene) Films"; Advanced Materials; 2008; 4 pages.

Koo, et al.; "Single-molecule detection of biomolecules by surface-enhanced coherent anti-Stokes Raman scattering"; Optics Letters; vol. 30; May 1, 2005; 3 pages.

Richards; "Nano-optics: Imaging beyond the Diffraction Limit, Fluorescence and Lifetime Modification, Surface Enhanced Raman Scattering"; http://www.opticalproteomics.org/research/nanooptics.php#sers; 2 pages.

Service; "Fast, Sensitive Scan Targets Anthrax"; http://www.sciencemag.org/cgi/content/full/308/5718/45?ck=nck; vol. 308; Apr. 1, 2005; 5 pages.

Stokes, et al.; "Detection of E. coli using a microfluidics-based antibody biochip detection system"; Advanced Monitoring Development Group; Nov. 13, 2000; 7 pages.

Taurozzi; "Sers-Active Silver Nanoparticle Arrays on Track Etch Membrane Support as Flow-through Water Quality Sensors"; http://aiche.confex.com/aiche/2006/techprogram/P59895.HTM; Nov. 15, 2006; 3 pages.

Tay; "Applications of Enhanced Raman Spectroscopy i Biological Sciences"; Institute for Microstructural Sciences; 2005; 12 pages.

Vo-Dinh; "Biosensors, Nanosensors and Biochips: Frontiers in Environmental and Medical Diagnostics"; Oak Ridge National Laboratory; The 1st International Symposium on Micro & Nano Technology; Mar. 2004; 6 pages.

Vo-Dinh, et al.; "Surface-enhanced Raman Scattering (SERS) Method and Instrumentation for Genomics and Biomedical Analysis"; Journal of Raman Spectroscopy; 1999; 9 pages.

Vo-Dinh, et al.; "Cancer gene detection using surface-enhanced Raman scattering (SERS)"; Journal of Raman Spectroscopy; Mar. 13, 2002; 6 pages.

Yakes, et al.; "Detection of *Mycobacterium avium* subsp. *paratuberculosis* by a Sonicate Immunoassay Based on Surface-Enhanced Raman Scattering"; Clinical and Vaccine Immunology; vol. 15; Feb. 2008; 8 pages.

Aizpurua, et al; "Optical Properties of Coupled Metallic Nanorods for Field-enhanced Spectroscopy"; The American Physical Society; 2005; 13 pages.

Chaney, et al; "Aligned Silver Nanorod Arrays Produce High Sensitivity Surface-enhanced Raman Spectroscopy Substrates"; American Institute of Physics; 2005; 3 pages.

Coldiron, et al; "Nanotechnology in Cancer"; http://www.concana.com/Nanotechnology.htm; Copyright 2007-2008; 5 pages.

Faulds, et al; "Evaluation of Surface-enhanced Resonance Raman Scattering for Quantitative DNA Analysis"; http://www.nano-biology.net/showabstract.php?pmid=14719891; 2004; 1 page.

Gu, et al; "Optimum Length of Silver Nanorods for Fabrication of Hot Spots"; American Chemical Society; 2007; 4 pages.

Hafner; "Plasmonics: Gold Nanoparticles are Shaped for Effect"; http://www.laserfocusworld.com/articles/article_display.html?id=252462; 2006; 4 pages.

Kim; "Surface Plasmon Resonances of Noble Metal Nanorods and Nanoparticles"; Sungkyunkwan University; May 29, 2007; 29 pages.

Murphy, et al; "Chemical Sensing and Imaging with Metallic Nanorods"; The Royal Society of Chemistry; 2008; 14 pages.

Nikoobakht, et al; "Surface-Enhanced raman Scattering Studies on Aggregated Gold Nanorods"; American Chemical Society; 2003; 7 pages.

Shuyi, et al; "An Approach to Self-Cleaning SERS Sensors by Arraying Au Nanorods on TiO2 Layer"; http://adsabs.harvard.edu/abs/2007SPIE.6647E..13L; 2007; 2 pages.

Suzuki, et al; "Physically Self-Assembled Ag nanorod Arrays for Tunable Plasmonic Sensors"; The Surface Science Society of Japan; 2005; 4 pages.

Suzuki, et al; "Vapor Phase Growth of al Whiskers Induced by Glancing Angle Deposition at High Temperature"; American Institute of Physics; 2006; 3 pages.

Uechi, et al; "Phtochemical and Analytical Applications of Gold Nanoparticles and Nanorods Utilizing Surface Plasmon Resonance"; Anal Bioanal Chem; 2008; 11 pages.

Yao, et al; "A Complementary Study of Surface-enhanced Raman Scattering and Metal Nanorod Arrays"; Pure Appl. Chem, vol. 72; 2000; 8 pages.

Yao, et al; "Electronic Properties of Metal Nanorods Probed by Surface-enhanced Raman Spectroscopy"; Chem. Commun.; The Royal Society of Chemistry; 2000; 2 pages.

Wang, et al.; Layer uniformity of glancing angle deposition; Vaccum; vol. 78, Issue 1, Apr. 4, 2005, pp. 107-111.

Schubert, et al.; Nanostructure fabrication by glancing angle ion beam assisted deposition of silicon; Applied Physics A: Materials Science & Processing; vol. 81, No. 3 / Aug. 2005.

Brett, et al.; Glancing Angle Deposition, An Overview of Thin Films and GLAD; http://www.ece.ualberta.ca/~glad/glad.html; 2006.

Gish, et al.; Evaluation of silver nanostructures fabricated using glancing angle deposition as localized surface plasmon resonance biosensors; Nanotech 2007 Conference Program Abstract.

Zhao, et al.; Designing Nanostructures by Glancing Angle Deposition; Proceedings of SPIE; vol. 5219; Nanotubes and Nanowires; Invited Paper, pp. 59-73.

Katherine A. Willets and Richard P. Van Duyne; Localized Surface Plasmon Resonance Spectroscopy and Sensing; Annual Review of Physical Chemistry; vol. 58: 267-297 (Volume publication date May 2007); First published online as a Review in Advance on Oct. 26, 2006.

Surface-Enhanced Vibrational Spectroscopy.

ARS Project: 408043—Annual Reports for 2004-2007; USDA Agricultural Research Service.

Big Discovery Symposium 2006; UC Santa Barbara; Epigenetic Enzymes and Therapies; slide show.

Kathy Kincade; Raman Spectroscopy: SERS and Silver Nanorods Quickly Reveal Viral Structures; Laser Focus World; Jan. 1, 2007.

Kathy Kincade; Optoelectronic Applications: Nanophotonics—An "Old" Technique Finds New Life in the Nano World; Laser Focus World; Oct. 1, 2006.

Kawai, et al.; Raman Spectroscopic Probes Withstand Hostile Environments; Laser Focus World; Jun. 1, 2005.

Amri, et al.; Adenine and RNA in Mineral Samples. Surface-Enhanced Raman Spectroscopy (SERS) for Picomole Detections; Spectrochimica Acta Part A 59 (2003) pp. 2645-2654.

Stuart, et al.; In Vivo Glucose Measurement by Surface-Enhanced Raman Spectroscopy; Anal. Chem. 2006, 78, pp. 7211-7215.

Faulds, et al.; DNA Detection by Surface Enhanced Resonance Raman Scattering (SERRS); The Royal Society of Chemistry 2005; Analyst, 2005, 130, pp. 1125-1131.

Bell, et al.; Surface-Enhanced Raman Spectroscopy (SERS) for Sub-Micromolar Detection of DNA/RNA Mononucleotides; J. Am. Chem. Soc. 2006, 128, pp. 15580-15581.

Yun Wei Charles Cao, et al.; Nanoparticles with Raman Spectroscopic Fingerprints for DNA and RNA Detection; Science, 297; 2002; pp. 1536-1540.

Mecham, et al.; Research on Bettering Surveillance of Arboviral Threats, Using West Nile Virus as a Model; USDA Agricultural Research Service; abstract.

Gish, et al.; Evaluation of Silver nanostructures Fabricated Using Glancing Angle Deposition as Localized Surface Plasmon Resonance Biosensors; The Nanotechnology Conference and Trade Show; Boston, Jun. 1-5, 2008; abstract.

Wang, et al.; Layer Uniformity of Glancing Angle Deposition; Vacuum; 78; 2005; pp. 107-111.

Schubert; Nanostructure Fabrication by Blaming Angle Ion Beam Assisted Deposition of Silicon; Appl. Physc. A81, 481-486 (2005).

Willets, et al.; Localized Surface Plasmon Resonance Spectroscopy and Sensing; Annu. Rev. Phys. Chem 2007; 52; 267-297.

Prokes, et al.; Enhanced Plasmon Coupling in Crossed Dielectric/Metal Nanowire Composite Geometries and Applications to Surface-Enhanced Raman Spectroscopy; Appl. Physc. Lett; 90; 2007; 3 pages.

D. Keith Roper; Determining Surface Plasmon Resonance Response Factors for Deposition onto Three-Dimensional Surfaces; Chemical Engineering Science; 62; 2007; pp. 1988-1996.

Takemoto, et al.; A Surface Plasmon Resonance Assay for the Binding of Influenza Virus Hemagglutinin to Its Sialic Acid Receptor; Virology; 217; 452-458 (1996) Article No. 0139.

Hardy, et al.; Valency of Antibody Binding to Enveloped Virus Particles as Determined by Surface Plasmon Resonance; Journal of Virology; Jan. 2003; p. 1649-1652; vol. 77, No. 2.

A Graded Improvement; Science, vol. 319; Feb. 29, 2008, p. 1163.

Kim; et al.; Light-Extraction Enhancement of GaInN Light-Emitting Diodes by Graded-Refractive-Index Indium Tin Oxide Anti-Reflection Contact; Adv. Mater. 2008, 20, pp. 801-804.

Robbie, et al.; Sculptured Thin Films and Glancing Angle Deposition: Growth Mechanics and Applications; J. Va. Sci. Technol. A 15(3), May/Jun. 1997; pp. 1460-1465.

Robbie, et al.; Fabrication of Thin Films With Highly Porous Microstructures; J. Va. Sci. Technol. A 13(3), May/Jun. 1995; pp. 1032-1035.

Robbie, et al.; First Thin Film Realization of a Helicoidal Bianisotropic Medium; J. Vac. Sc. Technol. A 13(6), Nov./Dec. 1995; pp. 2991-2993.

Office Action dated May 6, 2010 for U.S. Appl. No. 12/157,290.

\* cited by examiner

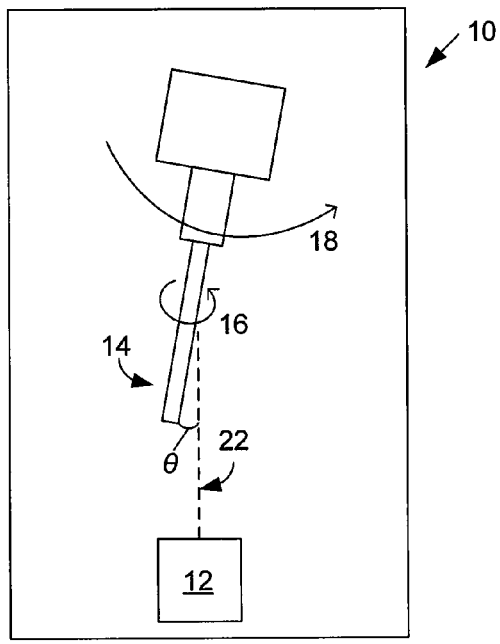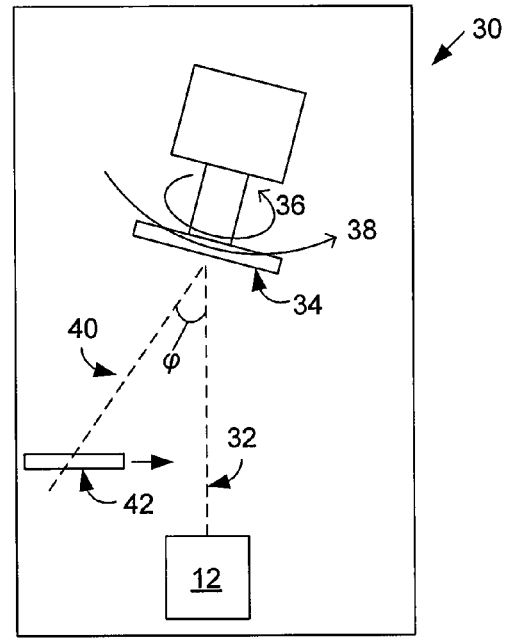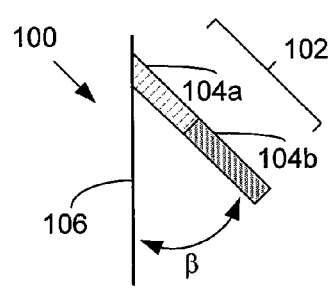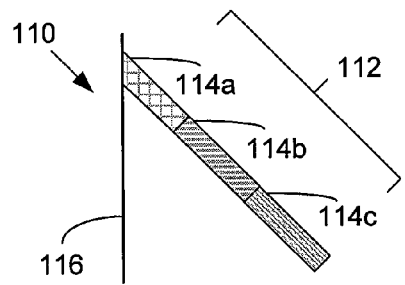
FIG. 1A  FIG. 1B
FIG. 2A  FIG. 2B

US 7,880,876 B2

METHODS OF USE FOR SURFACE ENHANCED RAMAN SPECTROSCOPY (SERS) SYSTEMS FOR THE DETECTION OF BACTERIA

CROSS-REFERENCE TO RELATED APPLICATION

This application is a continuation-in-part application, which claims priority to copending U.S. Utility patent application Ser. No. 11/376,661 entitled "SURFACED ENHANCED RAMAN SPECTROSCOPY (SERS) SYSTEMS, SUBSTRATES, FABRICATION THEREOF, AND METHODS OF USE THEREOF" filed on Mar. 15, 2006, now U.S. Pat. No. 7,738,096 which is a continuation-in-part of and claims priority to co-pending U.S. patent application entitled, "STRUCTURES HAVING ALIGNED NANORODS AND METHODS OF MAKING," having Ser. No. 11/256,395, filed Oct. 21, 2005, now U.S. Pat. No. 7,658,991, which claims priority to U.S. Provisional Application entitled, "DIRECT DEPOSITION OF ALIGNED NANOROD ARRAY ONTO CYLINDRICAL OBJECTS," having Ser. No. 60/620,810, filed Oct. 21, 2004, all of which are incorporated herein by reference. U.S. Utility patent application Ser. No. 11/376,661 also claims priority to U.S. Provisional Applications entitled "SURFACE ENHANCED RAMAN SPECTROSCOPY (SERS) SYSTEMS, SUBSTRATES, FABRICATION THEREOF, AND METHODS OF USE THEREOF," having Ser. No. 60/662,089, filed Mar. 15, 2005, and "SURFACE ENHANCED RAMAN SPECTROSCOPY (SERS) SYSTEMS, SUBSTRATES, FABRICATION THEREOF, AND METHODS OF USE THEREOF," having Ser. No. 60/703,110, filed Jul. 28, 2005, both of which are entirely incorporated herein by reference.

This application is a continuation-in-part application, which also claims priority to copending U.S. Utility patent application Ser. No. 11/495,980 entitled "SURFACE ENHANCED RAMAN SPECTROSCOPY (SERS) SYSTEMS AND METHODS OF USE THEREOF," filed on Jul. 28, 2006, now U.S. Pat No. 7,583,379, which claims priority to co-pending U.S. provisional application entitled "SURFACE ENHANCED RAMAN SPECTROSCOPY (SERS) SYSTEMS, SUBSTRATES, FABRICATION THEREOF, AND METHODS OF USE THEREOF," having Ser. No. 60/703,110, filed Jul. 28, 2005, both of which are entirely incorporated herein by reference.

U.S. Utility patent application Ser. No. 11/495,980 filed Jul. 28, 2006, is a continuation-in-part of and also claims priority to co-pending U.S. patent application entitled, "STRUCTURES HAVING ALIGNED NANORODS AND METHODS OF MAKING," having Ser. No. 11/256,395, filed Oct. 21, 2005, which claims priority to U.S. provisional application entitled, "DIRECT DEPOSITION OF ALIGNED NANOROD ARRAY ONTO CYLINDRICAL OBJECTS," having Ser. No. 60/620,810, filed Oct. 21, 2004, both of which are entirely incorporated herein by reference.

U.S. Utility patent application Ser. No. 11/495,980 is a continuation-in-part of and also claims priority to co-pending U.S. patent application entitled, "SURFACE ENHANCED RAMAN SPECTROSCOPY (SERS) SYSTEMS, SUBSTRATES, FABRICATION THEREOF, AND METHODS OF USE THEREOF" having Ser. No.:11/376,661, filed on Mar. 15, 2006, which claims priority to U.S. provisional application entitled "SURFACE ENHANCED RAMAN SPECTROSCOPY (SERS) SYSTEMS, SUBSTRATES, FABRICATION THEREOF, AND METHODS OF USE THEREOF," having Ser. No. 60/662,089, filed Mar. 15, 2005, both of which are entirely incorporated herein by reference.

In addition, this application claims priority to co-pending U.S. provisional application entitled "SURFACE ENHANCED RAMAN SPECTROSCOPY (SERS) SYSTEMS AND METHODS OF USE THEREOF" having Ser. No. 60/947,519 filed on Jul. 2, 2007, which is entirely incorporated herein by reference.

STATEMENT REGARDING FEDERALLY SPONSORED RESEARCH OR DEVELOPMENT

This invention was made with government support under ECS-0304340 and ECS-070178 awarded by the National Science Foundation, under EB001956 awarded by the National Institutes of Health, and through Cooperative Agreement W911NF-07-2-0065 with the U.S. Army Research Laboratory. The government has certain rights in the invention(s).

BACKGROUND

The discovery of single-molecule and single-nanoparticle surface-enhanced Raman scattering (SERS) has attracted considerable interest, both for fundamental studies of enhancement mechanisms and for potential applications in ultra sensitive optical detection and spectroscopy. A number of researchers have shown that the enhancement factors are as large as $10^{14}$-$10^{15}$, leading to Raman scattering cross sections that are comparable to or even larger than those of fluorescent organic dyes. This enormous enhancement allows spectroscopic detection and identification of single molecules located on the surface of single nanoparticles or at the junction of two particles at room temperature. Progress has been made concerning both the structural and mechanistic aspects of single-molecule SERS, but it is still unclear how this large enhancement effect might be exploited for applications in analytical chemistry, molecular biology, or medical diagnostics. One major problem is the intrinsic interfacial nature of SERS, which requires the molecules to adsorb on roughened metal surfaces. For biological molecules such as peptides, proteins, and nucleic acids, surface-enhanced Raman data are especially difficult to obtain, hard to interpret, and nearly impossible to reproduce. Therefore, a need in the industry exists to improve SERS data for biological molecules.

Various bacteria are responsible for numerous human diseases. For example, *Escherichia coli* can cause several intestinal and extra-intestinal infections such as urinary tract infections, meningitis, peritonitis, mastitis, septicemia, and Gram-negative pneumonia. Bacterial infections, such as these noted above, are the cause of millions of hospitalizations and thousands of deaths each year. Current detection and diagnostic methods for many bacterial pathogens are not sensitive enough for early and rapid detection. Thus, improved systems and methods for the detection of pathogens and other biomolecules are needed.

SUMMARY

SERS systems and methods for detecting an analyte of interest, particularly a biomolecule of interest, are disclosed. Briefly described, a representative embodiment of a method of detecting at least one bacterium in a sample, among others, includes: exposing a substrate having an array of nanorods on the substrate to the sample, where the sample includes at least one of a first bacterium and a second bacterium; and measuring a surface enhanced Raman spectroscopy (SERS) spectrum, where a SERS spectrum of the array of nanorods and the first bacteria is detectably different than a SERS spectrum of the array of nanorods and the second bacteria.

Briefly described, a representative embodiment of a method of detecting at least one biomolecule in a sample, among others, includes: attaching at least one first biomolecule to an array of nanorods on a substrate; exposing the substrate including the first biomolecule to the sample containing at least one of a second biomolecule and a third biomolecule; and measuring a surface enhanced Raman spectroscopy (SERS) spectrum, where a SERS spectrum of the array of nanorods and the first biomolecule is detectably different than a SERS spectrum of the array of nanorods, the first biomolecule, and the second biomolecule and a SERS spectrum of the array of nanorods, the first biomolecule, and the third biomolecule, and where the SERS spectrum of the array of nanorods, the first biomolecule, and the second biomolecule is detectably different than the SERS spectrum of the array of nanorods, the first biomolecule, and the third biomolecule.

Briefly described, a representative method of detecting at least one bacterium in a sample, among others, includes: exposing a substrate having an array of nanorods on the substrate to the sample, wherein the sample includes at least one of a first strain of *Escherichia coli* and a second strain of *Escherichia coli*; and measuring a surface enhanced Raman spectroscopy (SERS) spectrum, wherein a SERS spectrum of the array of nanorods and the first strain of *Escherichia coli* is detectably different than a SERS spectrum of the array of nanorods and the second strain of *Escherichia coli*.

Other aspects, compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 illustrates embodiments of modified oblique angle deposition (OAD) systems for a non-planar substrate (1A) and planar substrate (1B).

FIGS. 2A through 2E illustrate exemplary schematic representations of various combinations and shapes of nanostructures on SERS substrates.

FIG. 5A illustrates RMS roughness; FIG. 5B illustrates nanorod length; and FIG. 5C illustrates nanorod diameter as functions of normal deposition thickness.

FIG. 19A EC, *E. coli* O157:H7; ST, *S. typhimurium*; Mix, mix culture of *E. coli* O157:H7 and *S. typhimurium*. FIG. 19B EC, *E. coli* O157:H7; SA, *Staphylococcus aureus*; Mix, mix culture of *E. coli* O157:H7 and *Staphylococcus aureus*. Incident laser powers of 24 mW and collection time of 10 s were used to obtain these spectra. Spectra were offset vertically for display clarity.

DETAILED DESCRIPTION

Figure 2C:
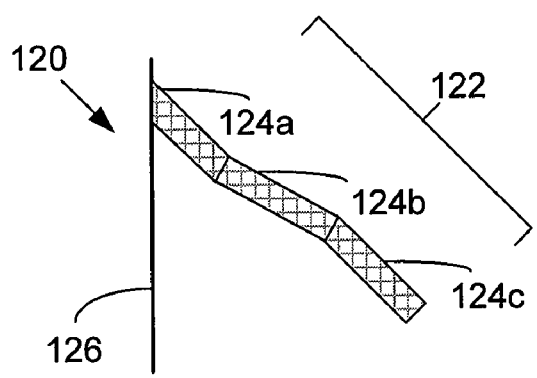

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

DEFINITIONS

Use of the phrase "biomolecule" is intended to encompass deoxyribonucleic acid (DNA), ribonucleic acid (RNA), nucleotides, oligonucleotides, nucleosides, proteins, peptides, polypeptides, selenoproteins, antibodies, protein complexes, combinations thereof, and the like. In particular, the biomolecule can include, but is not limited to, naturally occurring substances such as polypeptides, polynucleotides, lipids, fatty acids, glycoproteins, carbohydrates, fatty acids, fatty esters, macromolecular polypeptide complexes, vitamins, co-factors, whole cells, eukaryotic cells, prokaryotic cells, microorganisms such as viruses, bacteria, protozoa, archaea, fungi, algae, spores, apicomplexan, trematodes, nematodes, or combinations thereof.

In a preferred aspect, the biomolecule is bacteria. The terms "bacteria" or "bacterium" include, but are not limited to, Gram positive and Gram negative bacteria. Bacteria can include, but is not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia*, and *Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides*, and other *Nocardia* species, *Streptococcus* viridans group, *Peptococcus* species, *Peptostreptococcus* species, *Actinomyces israelii* and other *Actinomyces* species, and *Propionibacterium acnes, Clostridium tetani, Clostridium botulinum*, other *Clostridium* species, *Pseudomonas aeruginosa*, other *Pseudomonas* species, *Campylobacter* species, *Vibrio cholera, Ehrlichia* species, *Actinobacillus pleuropneumoniae, Pasteurella haemolytica, Pasteurella multocida*, other *Pasteurella* species, *Legionella pneumophila*, other *Legionella* species, *Salmonella typhi*, other *Salmonella* species, *Shigella* species *Brucella abortus*, other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi*, other *Hemophilus* species, *Yersinia pestis, Yersinia enterolitica*, other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium*, or any strain or variant thereof.

In another exemplary embodiment, the biomolecule is a surface molecule or surface antigen on the surface of a pathogen (e.g., a bacterial cell), or the biomolecule is a toxin or other byproduct of a pathogen (e.g., a toxin produced by a bacterial cell). Other examples of biomolecules are viral projections such as Hemagglutinin and Neuraminidase.

Use of the phrase "peptides", "polypeptide", or "protein" is intended to encompass a protein, a glycoprotein, a polypeptide, a peptide, fragments thereof and the like, whether isolated from nature, of viral, bacterial, plant, or animal (e.g., mammalian, such as human) origin, or synthetic, and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

Use of the phrase "polynucleotide" is intended to encompass DNA and RNA, whether isolated from nature, of viral, bacterial, plant or animal (e.g., mammalian, such as human) origin, or synthetic; whether single-stranded or double-stranded; or whether including naturally or non-naturally occurring nucleotides, or chemically modified. As used herein, "polynucleotides" include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base. An "oligonucleotide" generally refers to a nucleotide multimer of about 2 to 100 nucleotides in length, while a "polynucleotide" includes a nucleotide multimer having any number of nucleotides greater than 1, although they are often used interchangeably.

Use of the term "affinity" can include biological interactions and/or chemical interactions. The biological interactions can include, but are not limited to, bonding or hybridization among one or more biological functional groups located on the first biomolecule and the second biomolecule. In this regard, the first (or second) biomolecule can include one or more biological functional groups that selectively interact with one or more biological functional groups of the second (or first) biomolecule. The chemical interaction can include, but is not limited to, bonding among one or more functional groups (e.g., organic and/or inorganic functional groups) located on the biomolecules.

As used herein, the terms "antibody" and "antibodies" can include, but are not limited to, monoclonal antibodies, multispecific antibodies, human antibodies, humanized antibodies, camelised antibodies, chimeric antibodies, single-chain Fvs (scFv), single chain antibodies, Fab fragments, F(ab') fragments, disulfide-linked Fvs (sdFv), and anti-idiotypic (anti-Id) antibodies (e.g., anti-Id antibodies to antibodies of the disclosure), and epitope-binding fragments of any of the above. In particular, antibodies include immunoglobulin molecules and immunologically active fragments of immunoglobulin molecules (i.e., molecules that contain an antigen binding site). Immunoglobulin molecules can be of any type (e.g., IgG, IgE, IgM, IgD, IgA and IgY), class (e.g., IgG1, IgG2, IgG3, IgG4, IgA1 and IgA2) or subclass. The antibodies may be from any animal origin including birds and mammals (e.g., human, murine, donkey, sheep, rabbit, goat, guinea pig, camel, horse, or chicken). The antibodies may be monospecific, bispecific, trispecific, or of greater multispecificity.

Use of the term "types" with reference to bacteria is intended to include different families and/or genera of bacteria. Thus, for instance, the phrase "different types of bacteria" refers to bacteria from different genera or different families (e.g., *Escherichia* and *Salmonella*) and does not refer to different strains of bacteria of the same genus or species (e.g. Generic *E. coli* and *E. coli* O157:H7). Use of the term "strains" with reference to bacteria may refer to different strains/species of bacteria and/or to different sub-groups of bacteria within the same strain (e.g., different strains of *E. coli* such as Generic and O157:H7).

Discussion:

In accordance with the purpose(s) of the present disclosure, as embodied and broadly described herein, embodiments of the present disclosure, in one aspect, relate to surface-enhanced Raman spectroscopic (SERS) systems and methods of using the SERS systems to detect an analyte. The present disclosure provides, in general, methods and systems for the detection, differentiation, analysis, and/or quantification of a biomolecule (e.g., bacteria). One aspect, among others, provides methods and systems for the detection and differentiation of a biomolecule (e.g., bacteria) using SERS systems including a SERS substrate including an array of nanostructures.

In particular, the SERS system of the present disclosure can be used to determine the presence, qualitatively and/or quantitatively, and/or differentiating between one or more types of biomolecules, cells, toxins, drugs, viruses (e.g., different types, different strands of the same type, differences within strands of the same type, and the like), bacteria, explosives, nuclear wastes, contaminants, biohazards, and other chemical and biological compounds of interest. For clarity, this disclosure describes the use of the SERS system with biomolecules, but one skilled in the art would understand that the SERS system can be used to determine the presence, qualitatively and/or quantitatively, of other targets of interest such as those described above, to which a complimentary binding agent exists or can be designed. Embodiments of the present disclosure also relate to methods of using the SERS system to detect biomolecules in a sample. The SERS system can enhance the detection molecules (e.g., biomolecules) by a number of orders of magnitude (e.g., 5-12 orders of magnitude) in a reproducible manner.

In an embodiment, methods of the present disclosure provide for determining the presence, qualitatively and/or quantitatively, and distinguishing (e.g., a difference in the SERS spectra can be ascertained using methods such as, but not limited to, cluster analysis) between different types of bacteria. For example, embodiments of the present disclosure are able to distinguish among bacterium (e.g., between *E. coli* and *S. aureus*) based on at least the following: the ratio of the Adenine and Guanine band intensities.

In an embodiment, methods of the present disclosure provide for determining the presence, qualitatively and/or quantitatively, and differentiating (e.g., a difference in the SERS spectra can be ascertained using methods such as, but not limited to, cluster analysis) between different strains of the same bacteria, such as different strains of *Escherichia coli* (e.g., between Generic, O157:H7 and DH 5α), based on the variations in band frequencies of each SERS spectrum.

In an embodiment, methods of the present disclosure provide for determining the presence, qualitatively and/or quantitatively, and differentiating (e.g., a difference in the SERS spectra can be ascertained using methods such as, but not limited to, cluster analysis) between viable and non-viable cells.

In another embodiment, methods of the present disclosure provide for determining the presence, qualitatively and/or quantitatively, and differentiating (e.g., a difference in the SERS spectra can be ascertained using methods such as, but not limited to, cluster analysis) between different gram types.

In general, the SERS system includes an array of nanostructures on a substrate. In preferred embodiments, the nanostructure is a nanorod. In an exemplary embodiment, the nanostructure is functionalized with one or more binding agent(s) capable of binding (e.g., ionically, covalently, hydrogen binding, and the like) or otherwise associating (e.g., chemically, biologically, etc.) with one or more analytes (e.g., biomolecule(s)) of interest.

The nanostructures can include, but are not limited to, nanorods, nanowires, nanotubes, nanospirals, combinations thereof, and the like, and uniform arrays of each. The nanostructures (e.g., nanorods) can be fabricated of one or more materials such as, but not limited to, a metal, a metal oxide, a metal nitride, a metal oxynitride, a metal carbide, a doped material, a polymer, a multicomponent compound, a compound (e.g., a compound or precursor compound (organic or inorganic compound) including a metal, a metal oxide, a metal nitride, a metal oxynitride, a metal carbide, a doped material), and combinations thereof. The metals can include, but are not limited to, silver, nickel, aluminum, silicon, gold, platinum, palladium, titanium, copper, cobalt, zinc, other transition metals, composites thereof, oxides thereof, nitrides thereof, silicides thereof, phosphides ($P^{3-}$) thereof, oxynitrides thereof, carbides thereof, and combinations thereof. In particular, the materials can include one ore more of the following: silver, gold, nickel, silicon, germanium, silicon oxide, and titanium oxide. The composition of the nanorods is the same as that of the materials described herein or a combination of the materials described herein, or alternative layers of each.

In an embodiment of the SERS substrate of the present disclosure, the nanostructure is a nanorod. In particular embodiments, the nanorod is formed in a uniform and aligned array on the substrate. The nanorod can have the dimensions and characteristics as described below. In particular, the nanorods (e.g., silver, nickel, silicon, and titanium oxide) are disposed on a planar substrate, such as glass or silicon slide or disk, or a non-planar substrate, such as an optical fiber, or other cylindrically symmetric substrates.

A method of making a SERS substrate of the present disclosure includes providing a substrate and depositing the nanorods on the substrate by a modified oblique angle deposition (OAD) technique/system or glancing angle deposition (GLAD). In an embodiment of a modified OAD technique, the OAD system can include a two-axis substrate motion apparatus in a physical vapor deposition (PVD) system (e.g., thermal evaporation, e-beam evaporation, sputtering growth, pulsed laser deposition, and the like) that operates at temperatures lower than the melting point of the material used to form the nanostructures. In an embodiment, the substrate motion system provides two rotation movements: one is the polar rotation, which changes angle between the substrate surface normal and the vapor source direction, and one is the azimuthal rotation, where the sample rotates about its center axis of rotation (e.g., normal principle axis). In some embodiments, the nanorods are disposed on a thin film (e.g., silver, nickel, silicon, and titanium oxide) or a multilayer thin film (e.g., layers of silver, nickel, silicon, and titanium oxide, composites thereof, and nitrides thereof) that is deposited onto those substrates prior to nanorod deposition.

At least one advantage of using the OAD system is that the nanostructures (e.g., nanorods) can be formed at temperatures compatible with substrates such as, but not limited to, optical fibers, waveguides, and the like. This is in contrast to other techniques that operate under conditions (e.g., high temperatures) that are not compatible with many substrates of interest. Another advantage of using the OAD system is that catalysts are not needed to form the nanostructures, in contrast to currently used technologies. Since a vacuum system is used, the purity of the nanorods is very high, and the vacuum system is compatible with conventional microfabrication processes.

In some embodiments, the substrate is a planar (or flat) substrate, such as a silicon, quartz, or glass substrate. Planar substrates may also be made of materials including, but not limited to, semiconductors (e.g., Si, GaAs, GaAsP, and Ge), oxides (e.g., $SiO_2$, $Al_2O_3$), and polymers (e.g., polystyrene, polyacetylene, polyethylene, etc.). In other embodiments the substrate is a non-planar substrate such as a cylindrical or conical substrate (e.g., an optical fiber or pipette tip). The substrates can also be microfabricated or nanofabricated substrates, such as substrates with a regular array of micropatterns, such as a dot array, line array, or well array, or similar nanopatterns.

FIG. 1 illustrates an embodiment of an OAD system for a planar substrate 30 (FIG. 1B) and an embodiment of an OAD system for a non-planar substrate 10 (FIG. 1A). The OAD systems 10 and 30 include, but are not limited to, an evaporation source 12, a substrate 14 or 34, and a substrate manipulation mechanism (e.g., one or more motors) to move (e.g., rotate) the substrate relative to the evaporation source 12. A motor of the OAD system 10 can move the non-planar substrate 14 in a polar rotation 18, which changes the incident angle (θ) between the substrate rotating axis (e.g., center axis of rotation) and the vapor source direction (e.g., vapor arrival line 22). The OAD system 30 for the planar substrate 34 also includes a motor for moving the planar substrate 34 in a polar rotation 38, which changes the incident angle (φ) between the surface normal axis of the substrate (e.g., axis 40) and the vapor source direction (e.g., vapor arrival line 32).

Another motor of the OAD system 10 can move the substrate in an azimuthal rotation 16, where the sample rotates about its center axis of rotation (normal principle axis) to allow deposition of nanorods around the entire surface of the non-planar substrate 14. In the case of a planar substrate 34, while azimuthal rotation of the substrate is not required for deposition of the nanorods, the OAD system 30 may optionally include a second motor for rotating the planar substrate in an azimuthal rotation 36, which allows additional control over the shape of the nanorods. For both planar and non-planar substrates, varying the incident angles θ and φ and the rate and pattern of azimuthal rotation can result in various shapes, sizes, and/or distribution of nanorods on the substrate surface. The OAD systems 10 and 30 can also include appropriate vacuum pumps and electronic control equipment as are known in the art. Additional details regarding the OAD systems are described in the Examples below.

Embodiments of the OAD systems 10 and 30 can include a physical vapor deposition (PVD) system, such as thermal evaporation, e-beam evaporation, molecular beam epitaxy (MBE), sputtering growth, pulsed laser deposition, combinations thereof, and the like. In this embodiment, the PVD is a thermal evaporation source 12, where a material can be heated to an appropriate temperature to evaporate the material. The heating temperature depends primarily on the properties of the material to be deposited, but may also depend, at least in part, on the substrate 14 or 34, and other conditions in the OAD system. Typically, the temperature is less than the melting point (e.g., less than one-third of the melting point) of the material being evaporated.

In an alternative embodiment, the system can be adapted to include a Chemical Vapor Deposition (CVD) or a Plasma-Enhanced Chemical Vapor Deposition (PECVD) system. In such systems, an appropriate molecular precursor is evaporated at the source and undergoes decomposition at the surface of the substrate 14 or 34. The decomposition leads to the deposition of a material of interest onto the substrate 14 or 34 with concomitant elimination of molecular fragments, which can be easily purged from the system. CVD and PECVD allow for the single-step deposition of unitary- (e.g., metals), binary- (e.g., alloys, oxides, carbides), ternary- (e.g., $(Si,Ge)O_4$), and higher other compounds.

Modification of the system for use in conjunction with CVD and PECVD deposition techniques can be inferred from standard CVD and PECVD systems described in the art (e.g., D. M. Dobkin, M. K. Zuraw, *Principles of Chemical Vapor Deposition*, (2003) Springer, NY.; Srinivasan Sivaram, *Chemical Vapor Deposition: Thermal and plasma deposition of electronic materials (Electrical Engineering)*, (1995), Springer NY).

The OAD systems can operate at a substrate temperature less than the melting point of the material being evaporated. In particular, the substrates of the OAD systems can operate at or near room temperature, be cooled to liquid nitrogen temperature, or be heated to a temperature of about ⅓ of the melting temperature of the material being evaporated. Thus, substrates having a relatively low melting point (e.g., plastics such as those used in fiber optics) can be used, unlike other high temperature techniques. The OAD systems can operate at a pressure where the mean free path of the gas in the chamber during deposition is comparable or larger than the source-substrate distance.

The substrate 14 and/or 34 can be mounted or otherwise attached to an arm or other component in communication with the motors that move the substrate. In one embodiment, to deposit nanostructures (e.g., nanorods) onto a non-planar substrate 14, the substrate 14 is slightly rotated polarly in order to make an angle θ less than about 15° (e.g., θ less than about 12°, θ less than about 10°, θ less than about 8°, and θ less than about 5°; and where θ is from about θ, about 0 to 12°, about 0 to 10°, about 0 to 8°, and about 0 to 5°), with respect to the incoming vapor direction. Then, the source material is evaporated at a constant rate (e.g., the rate is about 0.1 nm/sec to 0.3 nm/sec, about 0.1 nm/sec to 0.6 nm/sec, about 0.1 nm/sec to 1 nm/sec, about 0.1 nm/sec to 1.5 nm/sec, and about 0.1 nm/sec to 2 nm/sec), or substantially constant rate, in the evaporation source 12, while the substrate 14 is rotated with a constant speed azimuthally (e.g., the speed is about 0.01 rev/sec to 0.05 rev/sec, about 0.01 rev/sec to 0.1 rev/sec, about 0.01 rev/sec to 0.2 rev/sec, and about 0.01 rev/sec to 0.4 rev/sec). The nanostructures of the evaporated material are thereby deposited (e.g., uniformly deposited) onto the sidewall (e.g., the inner and/or outer sidewall or selected portions thereof) of the substrate.

Such non-planar substrates are symmetrical about one center axis of rotation. The non-planar surface can be an inside surface and/or an outside surface of the substrate. The non-planar surface can include, but is not limited to, a cylindrical surface, a tapered surface, a conical surface, a tapered cylindrical surface, a cylindrical ringed substrate, and the like. The length of the substrate can be from about 1 mm to about 75 mm. The diameter of the substrate can be about 1 mm to about 75 mm. Exemplary substrates include, but are not limited to, optical fibers, waveguides, glass tubes, capillary tubes, metallic rods/tubes, and the like. Methods of forming nanostructure arrays on non-planar surfaces is described in greater detail in U.S. patent application Ser. No. 11/256,395, which is incorporated by reference herein.

In another embodiment, to deposit nanostructures (e.g., nanorods) onto a planar substrate 34 (e.g., a glass microscope slide), the substrate is mounted to the OAD device 30, as shown in FIG. 1B. Depending on the size of the OAD system, the size of the substrate may vary from about 1×1 mm² to about 30×30 cm². In some embodiments, it is preferable to deposit one or more thin film base layers of material (such as the materials described above for forming the nanostructures) on the substrate. This can be accomplished by first positioning the substrate at a normal incidence (e.g., φ=0°) to the evaporation source (e.g., where the substrate is face down to the evaporation source). A thin film base layer, or multilayer thin film base layer, may also be deposited on non-planar substrates by first positioning the substrate with the central axis of rotation perpendicular to the vapor line of arrival 22 from the evaporation source 12 (e.g., θ=90°), while continually rotating the substrate azimuthally at a constant rate of rotation. Additional details of the thin film are described below. In some embodiments, the thickness of the film is from about 10 nm to about 1000 nm; in a particular embodiment, it is between about 50 nm and about 500 nm. To deposit the nanorods on the planar substrate 34, the substrate is then rotated polarly in order to make an incident angle φ less than about 89° (e.g., where φ is from about 75° to 89°, about 80° to 86°, and about 86°), of the surface normal of the substrate with respect to the incoming vapor direction.

The nanorods are then deposited on the planar substrate by oblique angle vapor deposition. The source material is evaporated at a constant rate (e.g., the rate is about 0.1 nm/sec to 0.3 nm/sec, about 0.1 nm/sec to 0.6 nm/sec, about 0.1 nm/sec to 1 nm/sec, about 0.1 nm/sec to 1.5 nm/sec, and about 0.1 nm/sec to 2 nm/sec), or substantially constant rate, in the evaporation source 12, while the substrate 34 is optionally rotated azimuthally. The speed can be constant, or can vary, depending on the shape of the nanostructures desired (e.g., the speed is about 0.01 rev/sec to 0.05 rev/sec, about 0.01 rev/sec to 0.1 rev/sec, about 0.01 rev/sec to 0.2 rev/sec, and about 0.01 rev/sec to 0.4 rev/sec). The nanostructures of the evaporated material are thereby deposited (e.g., uniformly deposited) onto the surface of the substrate.

The temperature, the pressure, the deposition rate, the angle of vapor incidence, the evaporating material, and the speed and direction of the azimuthal rotation can be adjusted to control the properties of the nanostructures (e.g., the length, diameter, density, composition, and the like). Additional details regarding the process are described in the following Examples.

In some embodiments of methods of making the SERS substrates of the present disclosure, the nanorods are deposited in steps including exposing a first portion of a substrate to a metal vapor (e.g., via chemical metal vaporization) by opening a shutter 42 to a first setting. The first setting exposes a predetermined portion of the substrate. A first nanorod at a first position on the substrate is formed. The first nanorod grows to a first height (e.g., about 200 nanometers). Subsequently, the shutter is opened to a second setting, thereby exposing the first portion and a second portion to the metal vapor. A second nanorod is formed at a second position on the substrate. The second nanorod grows to the first height (e.g., about 200 nanometers). In this step the first nanorod grows to a second height (e.g., 400 nanometers), where the second height is about twice as high as the first height. This process can be repeated to expose a plurality of portions on the substrate to create a plurality of nanorods of various lengths on the substrate. For example, nanorods of the following lengths can be prepared: about 200 nanometers, about 400 nanometers, about 600 nanometers, about 800 nanometers, and about 1000 nanometers.

The length is the largest dimension of the nanostructure and is the dimension extending from the substrate (FIGS. 2A-E). The length/height of the nanorod can be from a few hundred nanometers or less to over a few thousand nanometers. In embodiments, the nanostructure can have a length of about 10 nm to 10000, about 10 nm to 5000 nm, about 10 nm to 4000 nm, about 10 nm to 3000 nm, about 10 nm to 2000 nm, about 10 nm to 1000 nm, about 10 nm to 500 nm, about 10 nm to 250 nm, about 10 nm to 100 nm, and about 10 nm to 50 nm. In particular, the nanostructures can have a length of about 100 nm to about 1500 nm. The length depends, at least in part, upon the deposition time, deposition rate, and the total amount of evaporating materials. The substrate can have nanorods of the same height or of varying heights on one or more portions of the substrate.

The diameter is the dimension perpendicular to the length. The diameter of the nanostructure is about 10 to 30 nm, about 10 to 60 nm, about 10 to 100 nm, about 10 to 150 nm. In particular, the nanorods can have a diameter of about 50 to 120 nm. One or more of the dimensions of the nanostructure could be controlled by the deposition conditions and the materials.

The substrate can have from tens to tens of thousands or more nanorods formed on the substrate. The array of nanostructures can be defined as having a distance of about 10 to 30 nm, about 10 to 60 nm, about 10 to 100 nm, about 10 to 150 nm, and about 10 to 200 nm, between each of the nanostructures. Alternatively, the array of nanostructures can be defined as having an average density of about 11 to 2500/μm². The number of nanorods, height and diameter of the nanorods, and the material that the nanorods are fabricated of will depend upon the specific application of the SERS system.

In embodiments of the SERS substrates of the present disclosure, as illustrated in FIG. 2A, the nanorods also have a tilt angle, β, formed between the nanostructure 102 and the substrate 106. The angle β is less than 90°, particularly from about 0° to about 50°, and in preferred embodiments can be from about 5° to about 20°, from about 15° to about 30°, and from about 25° to about 40°. The conditions and the materials used to prepare the nanostructure 102 can be used to determine/select the tilt angle. The tilt angle is important in creating SERS enhancement factors with sufficient sensitivity to detect binding of an analyte of interest to the SERS sensors of the present disclosure.

It should also be noted that the nanostructure could have multiple layers of different materials or alternating materials. FIGS. 2A and 2B illustrate nanostructures (e.g., nanorods) fabricated from two and three materials, respectively. In particular, FIG. 2A illustrates a nanostructure 102 disposed on a substrate 100 having a surface 106. The nanostructure 102 includes two layers of different materials 104a and 104b. The materials can be any combination of the materials described herein. The dimensions of the nanostructure 102 can include those described herein. In another embodiment, additional layers of materials can be formed on the nanostructure 102, as shown in FIG. 2B. For example, a repeating pattern of layers 104a and 104b can be created, or three layers 114a, 114b, and 114c of a nanostructure 112 can be created (FIG. 2B).

FIG. 2C illustrates a nanostructure 122 disposed on a substrate 120 having a surface 126. The nanostructure 122 includes three layers of one or more materials 124a, 124b, and 124c, in a zigzag pattern. The dimensions of the nanostructure 122 can include those described herein. The zigzag nanostructure can be created by changing the angle periodically from $\phi_1$ to $\phi_2$ (or from $\theta_1$ to $\theta_2$, in the case of non-planar substrates) during vapor deposition to change the tilt angle β of the nanostructure being formed. The material for layers 124a, 124b, and 124c can be the same material, or can be two or more different materials.

Figure 2D:
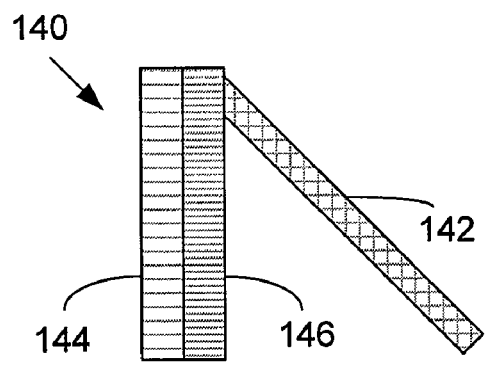

FIG. 2D illustrates a nanostructure 142 disposed on a layer 146 disposed on a substrate 140 having a surface 144. The layer 146 can be made of a material such as those described herein for forming the nanostructures, such as, but not limited to, a metal, a metal oxide, a metal nitride, a metal oxynitride, a doped material, a polymer, a multicomponent compound, and combinations thereof. The layer 146 can have a thickness of about 10 to 50 nm, about 10 to 100 nm, about 10 to 200 nm, about 10 to 500 nm, about 10 to 800 nm, about 10 to 1000 nm, and about 10 to 2000 nm. The dimensions of the nanostructure 142 can include those described herein. The layer 146 can be made by changing the incident angle φ first to 0° (in the case of non-planar substrates, θ to 90°), depositing a uniform first layer 146 by continuous azimuthal rotation. Then, angle φ is changed to a larger angle (or angle θ is changed to a smaller angle) to deposit nanostructure 142 on top of the film 146.

Figure 2E:
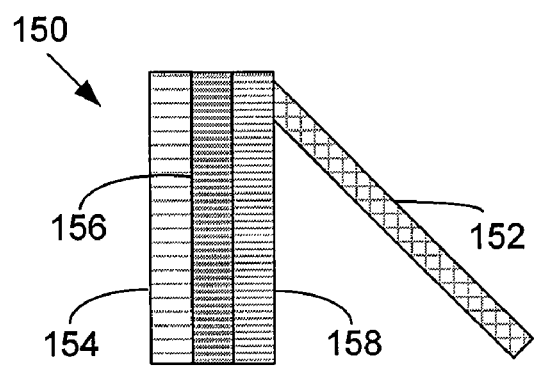

FIG. 2E illustrates a nanostructure 152 disposed on a second layer 158 disposed on a first layer 156 that is disposed on a substrate 150 having a cylindrical surface 154. The first and second layers 156 and 158 can each be made of a material, such as, but not limited to, a metal, a metal oxide, a metal nitride, a metal oxynitride, a doped material, a polymer, a multicomponent compound, and combinations thereof. The first and second layers 156 and 158 can each have a thickness of about 10 to 50 nm, about 10 to 100 nm, about 10 to 200 nm, about 10 to 500 nm, about 10 to 800 nm, about 10 to 1000 nm, and about 10 to 2000 nm. The dimensions of the nanostructure 152 can include those described herein. The first and second layers 156 and 158 can be made by changing the incident angle φ first to 0° (in the case of non-planar substrates, θ to 90°), depositing a uniform first layer 156 by continuous azimuthal rotation, and subsequently depositing a uniform second layer 158 by continuous azimuthal rotation. Then, angle φ is changed to a larger angle (or angle θ is changed to a smaller angle) to deposit nanostructure 152 on top of the second layer 158.

Additional combinations of uniform layer(s), nanorods with layers of multiple materials, and shaped nanorods are described in U.S. patent application Ser. No. 11/256,395, which is incorporated by reference herein. The nanostructures can also be formed in various shapes by varying the incident angle φ or θ and/or varying the speed, direction, and/or pattern of azimuthal rotation as described in Y. P. Zhao, D. X. Ye, Pei I. Wang, G. C. Wang, and T. M. Lu, "*Fabrication Si nano-columns and square springs on self-assembly colloid substrates,*" International Journal of Nanoscience 1, 87 (2002); and Y.-P. Zhao, D.-X. Ye, G.-C. Wang, and T.-M. Lu, "*Designing nanostructures by glancing angle deposition,*" SPIE Proceedings Vol. 5219, 59 (2003), which are hereby incorporated by reference herein in their entirety.

Figure 3A:
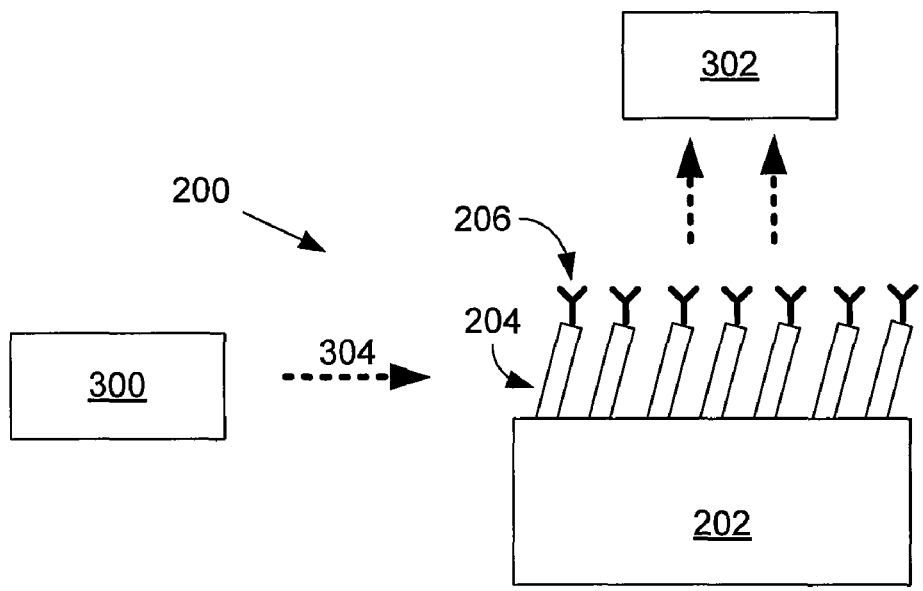
FIGS. 3A through 3B illustrate exemplary schematics of a SERS system according to the present disclosure having nanostructures deposited on the surface or portions of the surface of a substrate and a binding agent attached to the surface of the nanostructures (FIG. 3A), which is capable of binding a target analyte (FIG. 3B).

As illustrated in the SERS system 200 of FIG. 3A, once the nanorods 204 are formed on the substrate 202, a binding agent 206, such as a biomolecule, is disposed on one or more of the nanorods 204. The binding agent 206 is generally a biomolecule (as defined above), such as, a polynucleotide, polypeptide, carbohydrate, lipid, or the like. Exemplary polypeptide binding agents include, but are not limited to, antibodies or fragments thereof. The binding agent 206 can be attached/coupled to a surface of the nanostructure 204 using conventional linking chemistry (e.g., biologically (e.g., hybridization) and/or chemically (e.g., ionically or covalently)). For instance, the nanorods 204 can be functionalized by immobilizing the binding agent 206 (e.g., an antibody) on the nanorod surface by annealing to the metal (e.g., Ag or Au) surface of the nanorod via a linking agent (e.g., DSP (dithiobis(succinimidyl propionate)) or SAM (self-assembly monolayer)). Additional details regarding the disposition of the binding agent on the nanostructures are provided in the examples below.

A single type (e.g., the same polymer sequence) of binding agent 206 can be disposed or otherwise attached to the nanorods 204 on the substrate 202 (e.g., on the nanorods) or a plurality of types (e.g., two or more different polymer sequences) of binding agents can be disposed on the one or positions of the substrate.

Figure 3B:
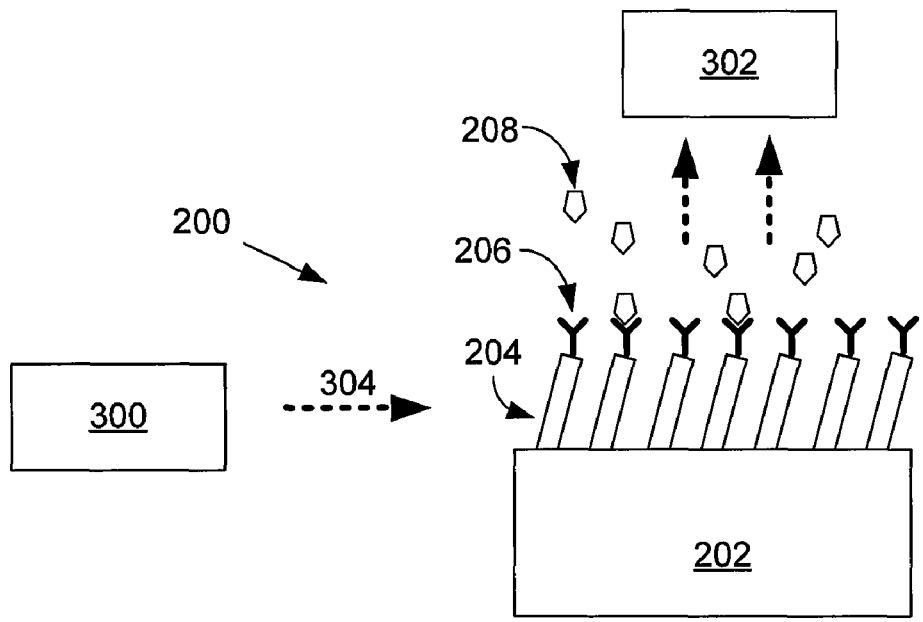

Typically, the binding agent 206, or first biomolecule, is disposed in an area of the substrate 202 having a plurality of nanorods 204. The array of nanorods 204 in combination with the first biomolecule 206 has a first measurable surface-enhanced Raman spectroscopic signature. Then, as illustrated in FIG. 3B, when an analyte of interest 208, such as a biomolecule (e.g., a second biomolecule), is introduced to the SERS system 200, the biomolecule 208 binds or otherwise interacts with the binding agent 206 bound to the nanostructure 204. Generally, the biomolecule 208 can be present or believed to be present in a sample, such as a gaseous, tissue or fluid sample. Exemplary samples include buccal cells, buffered solutions, saliva, sweat, tears, phlegm, urine, blood, plasma, cerebrospinal fluid, or combinations thereof.

The binding agent/first biomolecule 206 has an affinity for a second biomolecule 208. If the second biomolecule 208 bonds or otherwise attaches to the first biomolecule 206, the array of nanorods 204 in combination with the first biomolecule 206 and the second biomolecule 208 has a second measurable surface-enhanced Raman spectroscopic signature that is different (e.g., a statistically significant difference is enough of a difference to distinguish among the spectra, such as about 0.1%, 1%, 3%, 5%, 10%, 15%, 20%, 25%, 30%, or 40% or more difference between the spectrum of the first biomolecule and the spectrum of the second biomolecule) than first measurable surface-enhanced Raman spectroscopic signature. Therefore, the interaction of the first biomolecule 206 and the second biomolecule 208 can be measured using the SERS system 200. Additional details regarding the detection of a second biomolecule binding event by measuring the surface-enhanced Raman spectroscopic signatures are provided in the Examples below.

Figure 3C:
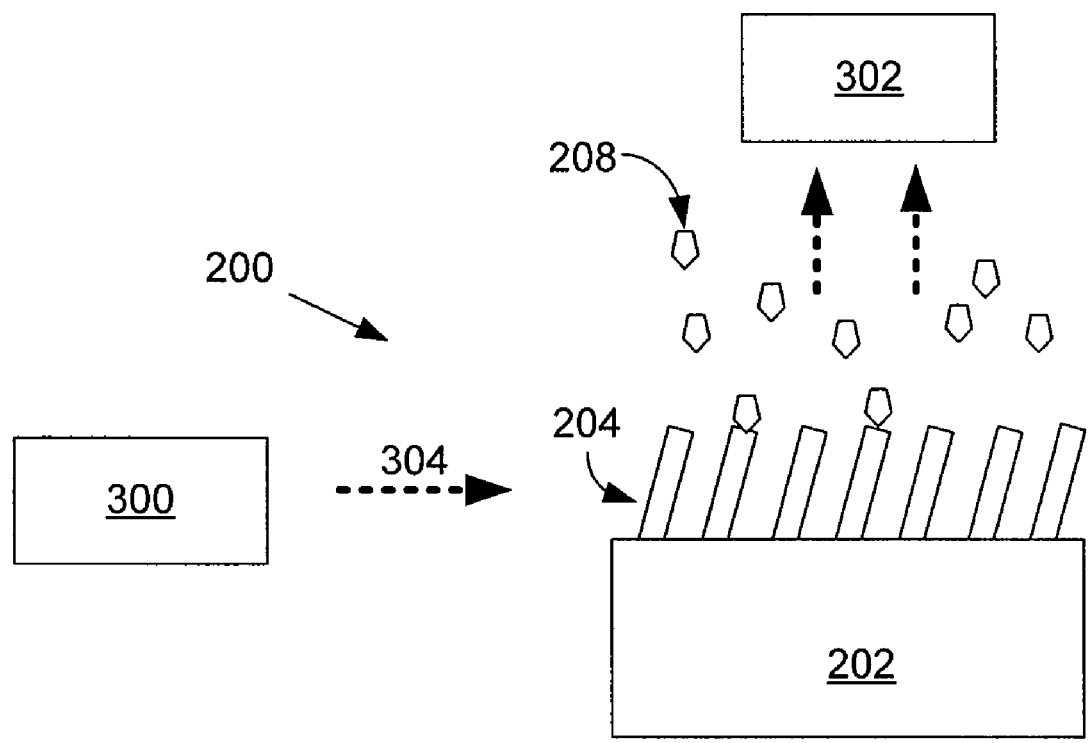
FIG. 3C is an exemplary schematic illustration of an embodiment of a SERS system according to the present disclosure having nanostructures deposited on the surface or portions of the surface of a substrate, which are capable of binding and detecting a target analyte directly, without a binding agent.

In other embodiments of the SERS system 200, as illustrated in FIG. 3C, the analyte of interest 208 (e.g., a biomolecule including, but not limited to, a virus, bacterium, or other pathogen or fragment thereof) can be disposed directly on the nanorods 204. A particular biomolecule of interest can be detected because individual biomolecules of interest have a unique SERS spectra that is detectably different, and thus distinguishable, from the SERS spectra of other biomolecules. For example, individual strains of *Escherichia coli* can be distinguished in this manner as depicted in Example 3, FIG. 11. Thus, individual biomolecules, such as bacteria, have a unique SERS "fingerprint" that allow a particular biomolecule of interest to be distinguished from other biomolecules or background media.

Embodiments of the SERS system 200, also include an excitation source 300. The excitation source includes, but is not limited to, illumination sources such as a diode laser and an optical fiber laser, dye laser, solid state laser. In some embodiments, the excitation source 300 provides a stream of incident light 304 directed to the SERS substrate 202 to provide excitation for generating the Raman signal. In preferred embodiments, the incident light 304 is perpendicular to the nanorods 204, as illustrated in FIG. 3B. The SERS system 200, also may include a data collection and analysis system, such as an optical data collection port 302 for collecting the Raman signal produced by the excitation of the SERS substrate and a system for producing the SERS spectra. Additional details regarding the excitation source and SERS data collection and analysis systems are provided in the examples below.

As mentioned above, embodiments of the present disclosure provide SERS systems and methods for determining the presence, qualitatively and/or quantitatively, and distinguishing between different types of bacterium. In general, the SERS systems and methods of use thereof can measure SERS spectra of different bacteria. The SERS system can measure detectably different (e.g., a difference in the SERS spectra can be ascertained using methods such as, but not limited to, cluster analysis) features between the bacteria. In particular, each bacterium can have a measurable surface-enhanced Raman spectroscopic signature, where the signatures of each bacterium are distinguishable and include detectably different features.

As mentioned above, embodiments of the present disclosure provide SERS systems and methods for determining the presence, qualitatively and/or quantitatively, and distinguishing between different strains of bacterium. In general, the SERS systems and methods of use thereof can measure SERS spectra of different strains of bacteria. The SERS system can measure detectably different (e.g., a difference in the SERS spectra can be ascertained using methods such as, but not limited to, cluster analysis) features between the bacterial strains. In particular, each bacterial strain can have a measurable surface-enhanced Raman spectroscopic signature, where the signatures of each bacterial strain are distinguishable and include detectably different features.

Embodiments of the present disclosure include a method of detecting at least one bacterium in a sample, comprising exposing a substrate having an array of nanorods on the substrate to the sample, where the sample includes at least one of a first bacterium and a second bacterium and measuring a surface enhanced Raman spectroscopy (SERS) spectrum, where a SERS spectrum of the array of nanorods and the first bacteria is detectably different than a SERS spectrum of the array of nanorods and the second bacteria. In an embodiment, the first bacterium and the second bacterium are the same type of bacteria but comprise different strains, where the first bacterial strain has a first measurable surface-enhance Raman spectroscopic signature, the second bacterial strain has a second measurable surface-enhanced Raman spectroscopic signature, and the first measurable surface-enhanced spectroscopic signature and the second measurable surface-enhanced Raman spectroscopic signature are distinguishable.

In an embodiment, each of the first bacterium and the second bacterium are selected from *Escherichia*. In another embodiment, each of the first and the second bacteria is selected from *Escherichia adecarboxylata*, *Escherichia albertii*, *Escherichia blattae*, *Escherichia coli*, *Escherichia fergusonii*, *Escherichia hermannii*, or *Escherichia vulneris*. In an embodiment, the first bacterium and the second bacterium comprise different strains of *Escherichia coli*.

In an embodiment, methods of the present disclosure provide for determining the presence, qualitatively and/or quantitatively, and differentiating (e.g., a difference in the SERS spectra can be ascertained using methods such as, but not limited to, cluster analysis) between different strains of the same bacteria, such as different strains of *Escherichia coli* (e.g., between Generic, O157:H7, and DH 5α)

EXAMPLES

Example 1

Sample Preparation

All of the samples were prepared using an electron beam/sputtering evaporation system (E-beam) that was custom built by Torr International. A schematic of the set-up is shown in FIG. 1A. A glass microscope slide with size 1×3" and 1 mm thick (Gold Seal®) was used as a substrate 34. A custom shutter 42 was built that could be controlled externally by a feed through, and the shutter was used to selectively reveal increasing portions of the substrate 34 during the deposition process. This method can produce one single sample with 6 different active areas. As an example, one particular sample had a 50 nm thin film deposited at normal incidence and then it was rotated to an incident angle 4 of 86°. Then nanorods were deposited in steps of 200 nm; i.e., the shutter 42 was opened partially and 200 nm was deposited, then the shutter was opened slightly more exposing more of the substrate and another 200 nm was deposited while keeping the previously exposed area still open making two sections one with 200 nm rods and one with 400 nm. This was repeated until a total of 1000 nm was reached for the first open area. The purpose of this particular setup is to achieve an environment in which all experimental conditions are the same for each different rod length. In a conventional setup (one rod length per sample, per run), the time needed to complete the experiments would be 5 days opposed to 1 day.

The background pressure was $4.5 \times 10^{-6}$ Torr for, and the base temperature was 48.5° C. The source to substrate distance was approximately 12". The deposition was divided into two sections: the first was depositing the 50 nm thin film at a rate of 0.4 Å/s, and the second was depositing the rods at a rate of 2.0 Å/s. The schematic of the resulting film and nanorod is shown in FIG. 2D.

Figure 4:
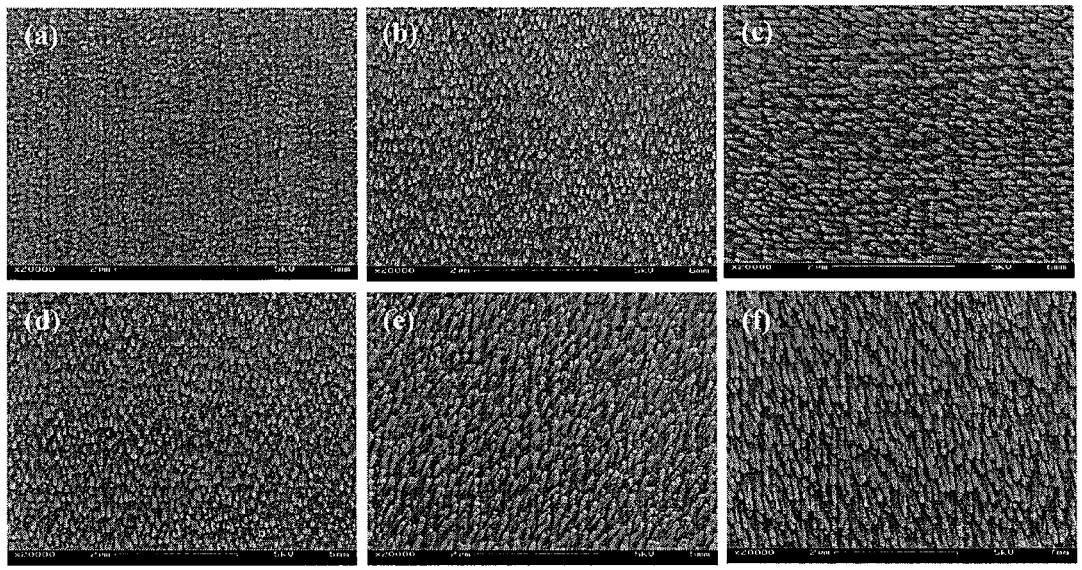
FIG. 4 illustrates SEM images of various length nanorods on a planar substrate.
Figure 5:
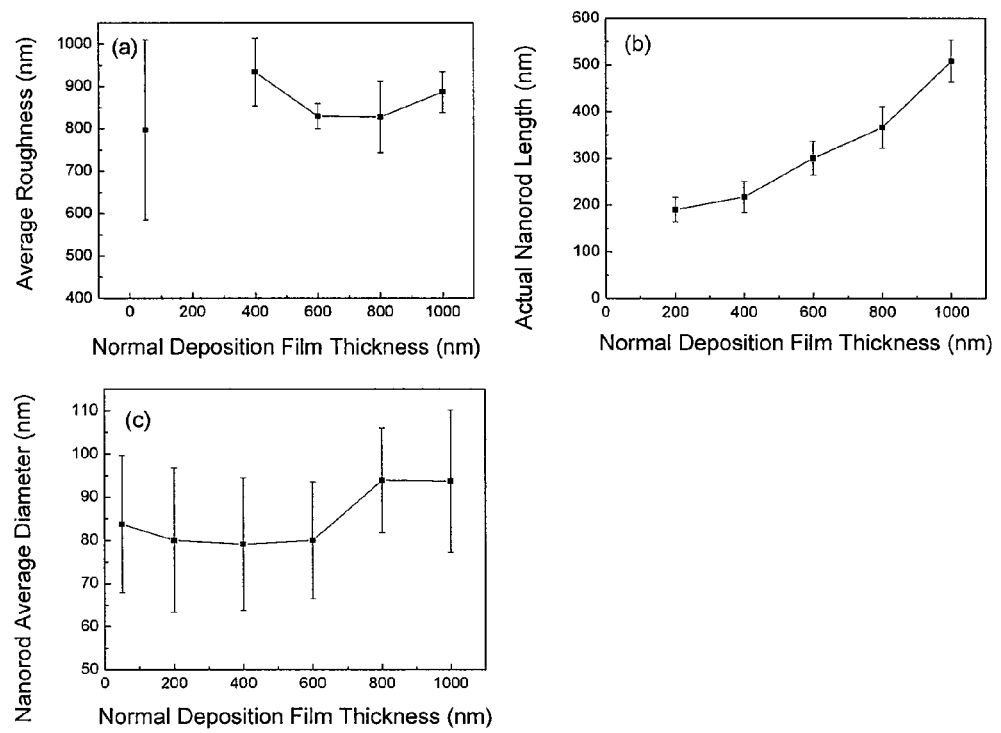
FIGS. 5A through 5C illustrates various nanorod parameters.

The actual length and density of the rods were measured using Scanning Electron Microscopy (SEM), and the roughness of the surfaces was measured using Atomic Force Microscopy (AFM). FIG. 4 shows the SEM images of the nanorods at different section on the substrate. The average roughness, diameters, and actual lengths of each section of nanorods are displayed in the graphs illustrated in FIG. 5.

The actual rod length denotes the fact that when depositing at an angle of about 86°, the deposition rate displayed by the thickness monitor is not the same as the amount of material actually deposited onto the substrate due to a reduced flux. The diameter is representative of the average width of the tips of several hundreds of rods at a given length.

SERS Measurements:

Surface Enhanced Raman spectra were acquired using a Kaiser Optical Systems confocal Raman microscope (Kaiser Optical Systems Incorporated, Ann Arbor, Mich.) equipped with a liquid nitrogen cooled Charge Coupled Device (CCD) camera (Princeton, Instruments, Trenton, N.J.). The spectrograph used was a Holospec f/1.8-NIR spectrometer equipped with a HoloPlex grating that simultaneously measures the range of 100 to 3450 $cm^{-1}$ at an excitation wavelength of 785 nm illumination supplied by a Coherent Radiation 899 Ti:Sapphire Ring Laser (Coherent, Santa Clara, Calif.) pumped by a Coherent Radiation Innova 300 Series Ar$^+$ laser (Coherent, Santa Clara, Calif.). SERS spectra were collected with ~20 mW laser power at the sample under the microscope objective.

All spectra were collected using the Holograms 4.0 software supplied by the manufacturer. Post processing of the collected spectra was performed using GRAMS32/AI spectral software package (Galactic Industries, Nashua, N.H.). Center of Gravity calculations were made using a GRAMS32 based program written in our laboratory (R. A. Dluhy, unpublished). All spectra were baseline corrected for clarity.

Figure 6:
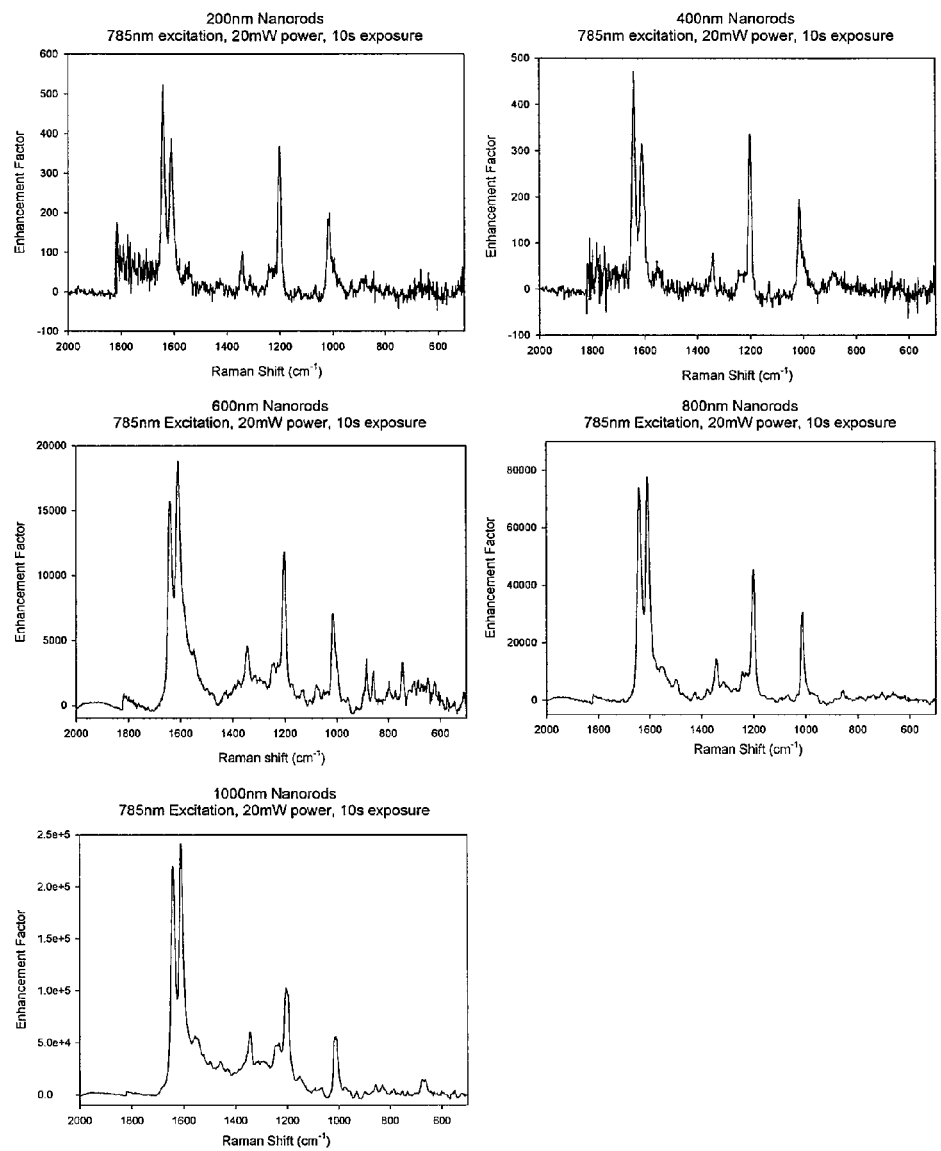
FIG. 6 illustrates SERS spectra for samples having various length nanorods.

The molecular probe used in this study was trans-1,2-bis (4-pyridyl)ethene (BPE, Aldrich, 99.9+%). BPE solutions were prepared by sequential dilution of HPLC grade methanol (Aldrich). BPE solution was applied to each of the SERS substrates and allowed to dry before the acquisition of spectra. The concentration of the BPE and the volume applied were calculated so as to produce a surface coverage of about 0.21 monolayers (assuming $7\times10^{14}$ BPE molecules per $cm^2$ in a monolayer). It has been observed that at greater monolayer coverage the SERS intensity drops off significantly. This drop-off has been attributed to inter-adsorbate interactions and coverage-dependent dielectric interactions. Spectra were acquired for about 10 s and obtained for multiple spots on each substrate. BPE was chosen as the probe to calculate enhancement factors because of its high Raman scattering cross-section and its ability to adsorb strongly and irreversibly to the Ag substrate. The 1200 $cm^{-1}$ peak of BPE was chosen for the quantification because of its relative insensitivity to molecular orientation on a Ag surface. FIG. 6 shows the SERS spectroscopy of different samples with different nanorod lengths.

Calculation of Surface Enhancement Factor

The Surface Enhancement Factor (SEF) is defined as the ratio of the integrated intensities contributed by the molecules on the surface and in the solution, respectively. where $I_{surf}$ and $I_{bulk}$ denote the integrated intensities for the 1200 $cm^{-1}$ band of the BPE adsorbed on the Ag surface and BPE in solution respectively, whereas $N_{surf}$ and $N_{bulk}$ represent the corresponding number of BPE molecules excited by the laser beam. Thus from the surface Raman signal detected, the solution spectrum, and the solution concentration, the Surface Enhancement Factor was calculated for the different SERS substrates.

$N_{surf}$ was calculated using the following approximation:

$$N_{surf}=A_{substrate}\times0.21\times7\times10^{14}\times\pi a^2$$

where $A_{substrate}$ is the geometric area of the SERS substrate (in $cm^2$); and a is the radius of the laser focal spot.

$N_{bulk}$ was calculated using the following approximation:

$$N_{bulk}=\pi a^2 hcN_A$$

where c is the concentration of the BPE solution in the cuvette; h (in μm) is the confocal depth; and $N_A$ is the Avogadro number.

$I_{surf}$ and $I_{bulk}$ were calculated from the integrated area under the 1200 $cm^{-1}$ band in the BPE spectrum using a Center of Gravity algorithm written by the present investigators in the GRAMS32 environment.

Figure 7:
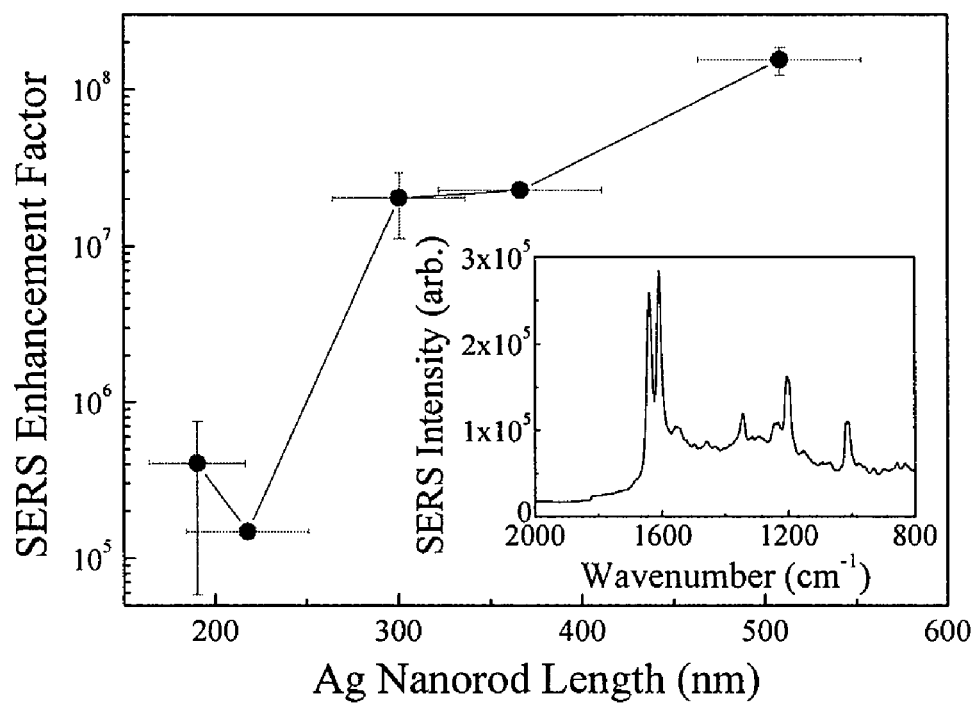
FIG. 7 illustrates a graph of the SERS enhancement factor relative to the length of the nanorods.
Figure 8:
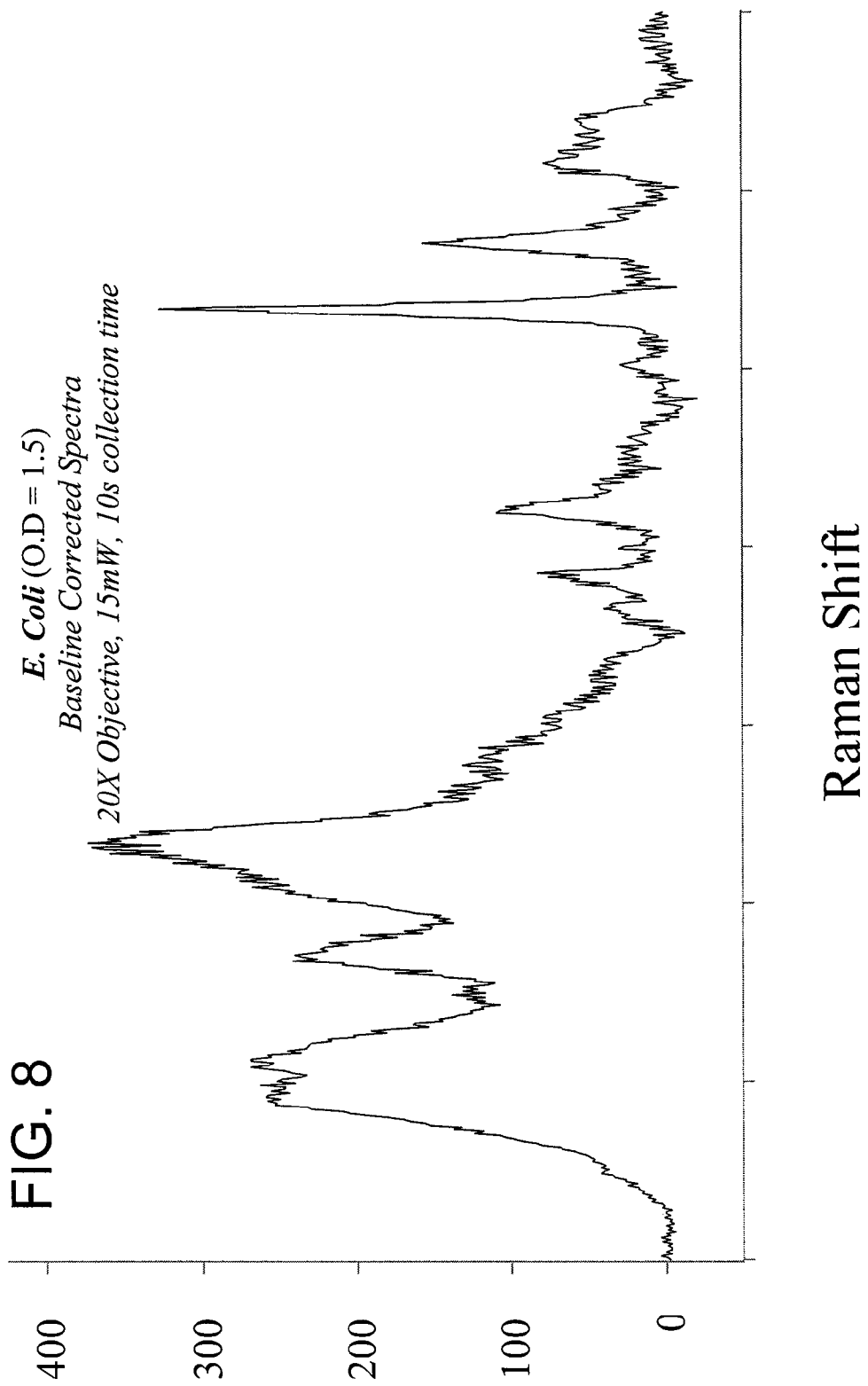
FIG. 8 illustrates a representative SERS spectrum of *E. coli*.
Figure 9:
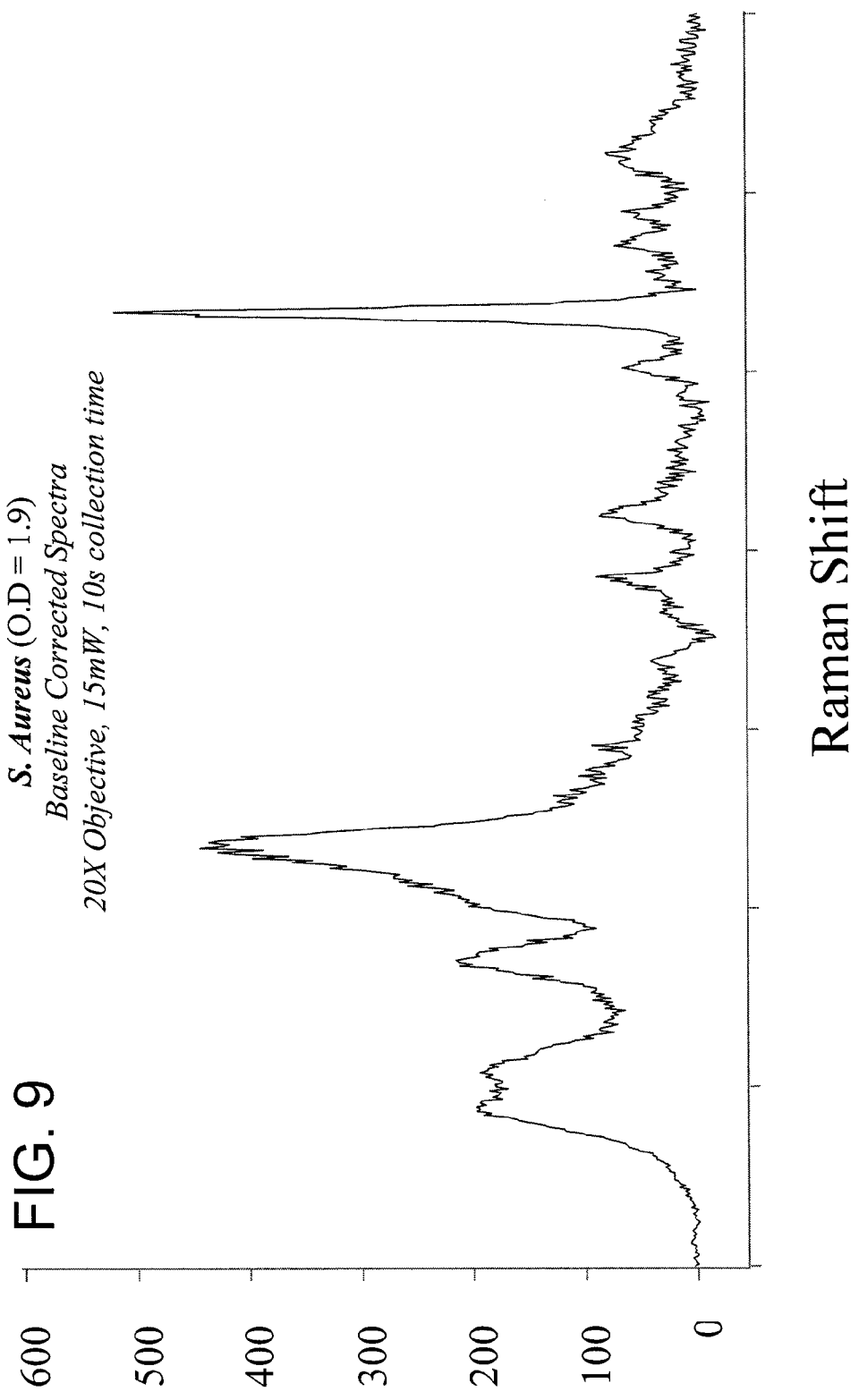
FIG. 9 illustrates a representative SERS spectrum of *S. aureus*.
Figure 10:
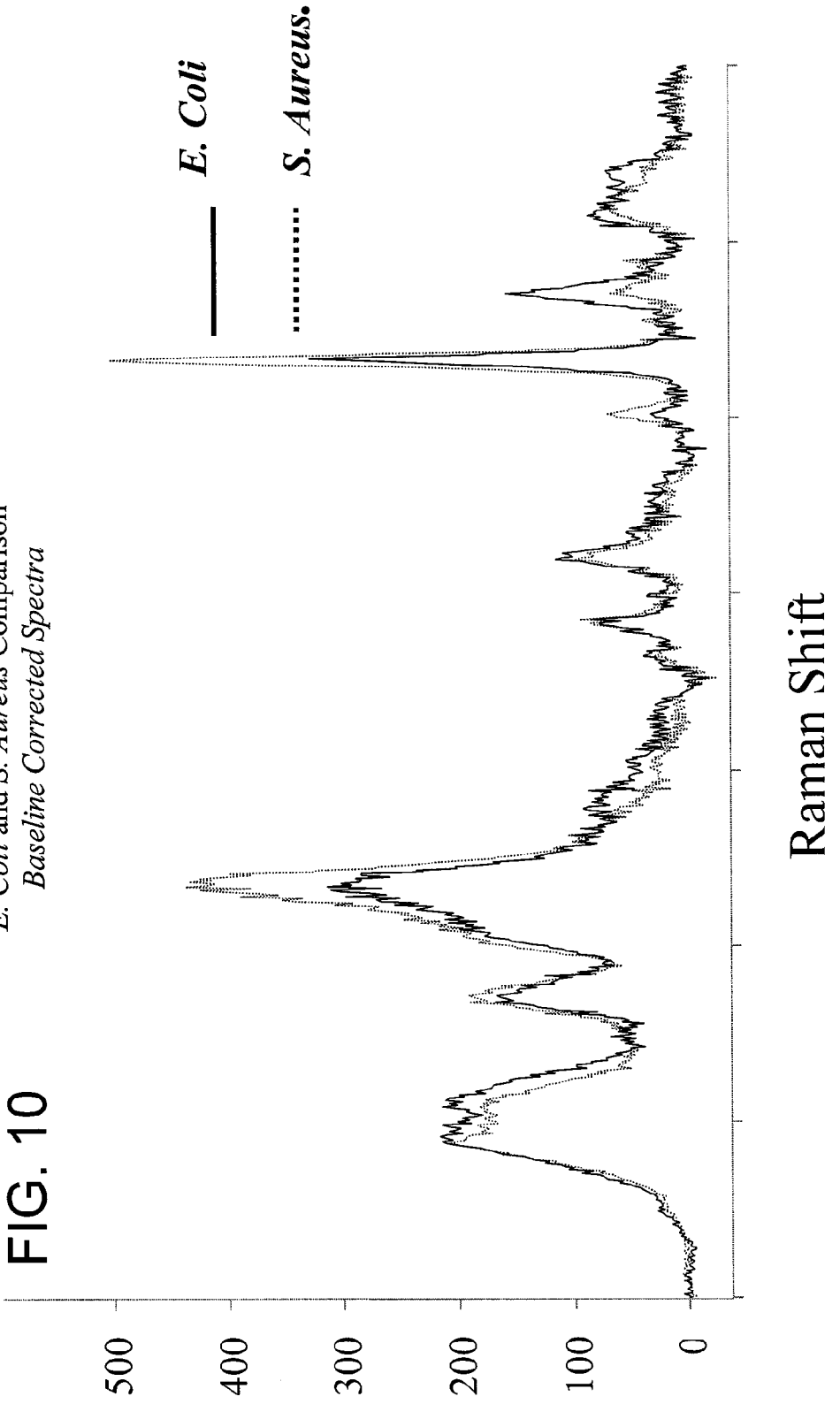
FIG. 10 illustrates a representative SERS spectrum comparison of the *E. coli* and *S. aureus*. It should be noted that embodiments of the present disclosure can distinguish between *E. coli* and *S. aureus* based on at least the following: (1) The ratio of the Adenine (734 cm-1) and Guanine (685 cm-1) band intensities A/G for *E. coli* is ~2.1 while for *S. aureus* ~8.5 (Based on ratio calculated for 6 different spectra on a single substrate); and (2) Region between 500 cm-1-600 cm-1.

Surface Enhancement Factors (EF) were calculated for each of the spectra collected on all the SERS substrates and were plotted with error bars against the nanorod length. FIG. 7 shows the actual EF versus nanorod length.

Example 2

SERS can Detect Different Types of Bacterium

SERS was used to analyze the Gram negative bacterium *Escherichia coli* and the Gram positive bacterium, *Staphylococcus aureus*. The bacterial cells were grown to an $OD_{600}$ of 1.5 for *E. coli* and 1.9 in the case of the *S. aureus*, washed five times with water and re-suspended in ~1 mL water. About 0.5 μL of the suspension was spotted onto the SERS substrate and spectra were collected after 60 minutes. SERS spectra were obtained with a laser power of ~15 mW at 785 nm with collection times of 10 s. The displayed spectra are representative of data collected form multiple spots on the substrate.

The main bands in both the SERS spectra arise from nucleic acids, surface proteins, amino acids and lipid components of the cell membrane. The spectra are similar looking with the main difference being the relative intensities of the bands at 658 $cm^{-1}$ (Guanine), 733 $cm^{-1}$ (Adenine) and 797 $cm^{-1}$. There is also a difference in the spectral region between 500 $cm^{-1}$ and 600 $cm^{-1}$. It is possible to calculate the band ratios of the Adenine and Guanine bands to discriminate between the two bacteria; while *E. coli* has a A/G ratio of ~2.1, the ratio in the case of *S. aureus* is ~8.5.

It should be noted that the bacteria gave very good SERS response with the Ag nanorod substrate. Embodiments of the present disclosure are able to distinguish between *E. coli* and *S. aureus* based on at least the following: the ratio of the Adenine and Guanine band intensities, and A/G for *E. coli* is ~2.1 while for *S. aureus* ~8.5 (based on ratio calculated for 6 different spectra on a single substrate) in the region between 500 $cm^{-1}$-600 $cm^{-1}$. The SERS bands due to surface protein secondary/tertiary structure between 1500-1700 $cm^{-1}$ are similar. The background signal from the substrate is also present in this region so there is some contribution. The *E. coli* spectra look similar to what has been published in the literature. (+/−a couple of bands).

Example 3

Using Ag Nanorod-Based SERS to Detect Different Strains of *Escherichia coli*

The present example presents experiments demonstrating the use of embodiments of the SERS system of the present disclosure (Ag nanorod substrates) as a rapid, sensitive and discriminatory method for detection and differentiation of *Escherichia coli* (*E. coli*) strains.

*Escherichia coli* Preparation Methods

Cell Preparation

*E. coli* O157:H7 (ATCC 43888) as target bacteria are obtained from American Type Culture Collection (Rockville, Md.). The pure culture is grown in Trypticase soy broth (TSB, Difco) over night in a shaker incubator at 37° C., 240 rev/min before use. The culture is centrifuged at 10,000 rpm for 10 min and the supernatant are discarded. Pellet is resuspended and washed three times. Bacterial populations are determined by the conventional surface plating-count method. Desired dilutions are made in sterilized DI water. DI water served as control.

SERS Measurements SERS spectra are acquired using a HRC-10HT Raman analyzer system (Enware Optronics Inc. Irvine, Calif.). This system was made up of a diode laser, spectrometer, integrated Raman probe head for both excitation and collection, and separate excitation and collection fibers. The excitation source was a frequency stabilized, narrow linewidth near IR diode laser with a wavelength of 785 nm. The excitation laser beam coupled to a 100 µm fiber was focused onto the substrate through the Raman probe head and was unpolarized at the sample. The focal length of the Raman probe was 6 mm, and the diameter of the focal spot was 1 mm. The Raman signal from the substrate was collected by the same Raman probe head and was coupled to a 200 µm collection fiber, which delivered the signal to the spectrometer equipped with a charge coupled device (CCD) detector. The laser power at the sample was 69 mW and spectra were acquired with a 10 s integration. A 5.0-µL aliquot of bacteria solution was applied to the Ag nanorod substrate and allowed to evaporate at room temperature prior to spectrum acquisition. SERS spectra were collected from 6 different spots across the substrate.

Results

SERS Spectra

Prior to data collection the substrates were stored in a relatively clean environment at room temperature to avoid any changes in surface morphology due to temperature or atmospheric humidity. 5 µl of bacteria solutions were applied onto silver nanorod substrates and allowed to dry before SERS measurement. Spectra were collected from multiple spots. The raw SERS spectra for each sample differ in the number of scattered bands, band locations, and the magnitude of the bands. Variations in band frequencies reflect compositional and structural differences in the bacteria while differences in peak intensities are a result of slight differences in the morphology of the SERS substrates. To eliminate spectral discrepancies caused by the substrates, each SERS spectrum was normalized with respect to its most intense peak. This preprocessing step allows direct comparison of peak intensities between spectra obtained from different substrates.

Figure 11:
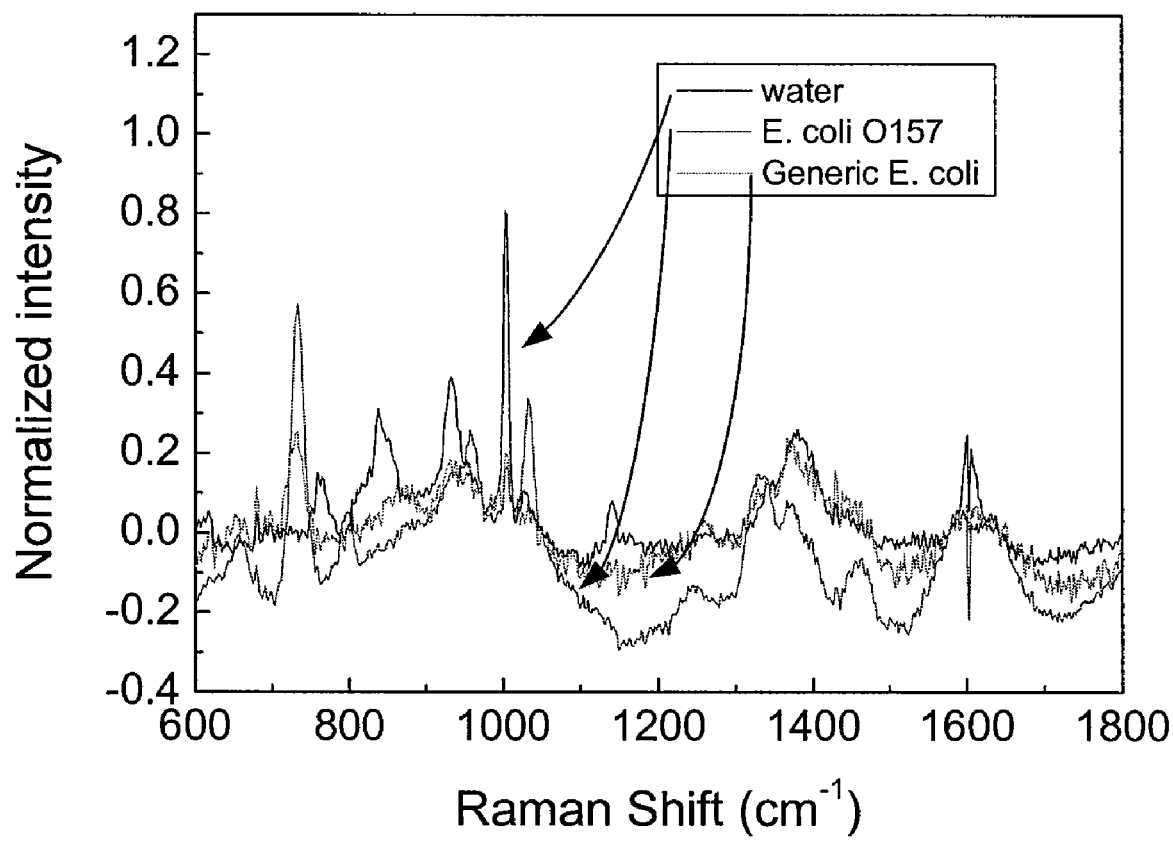
FIG. 11 illustrates the average SERS signal for water (control), Generic *E. coli*, and *E. coli* O157:H7 between 600-1800 $cm^{-1}$.
Figure 12:
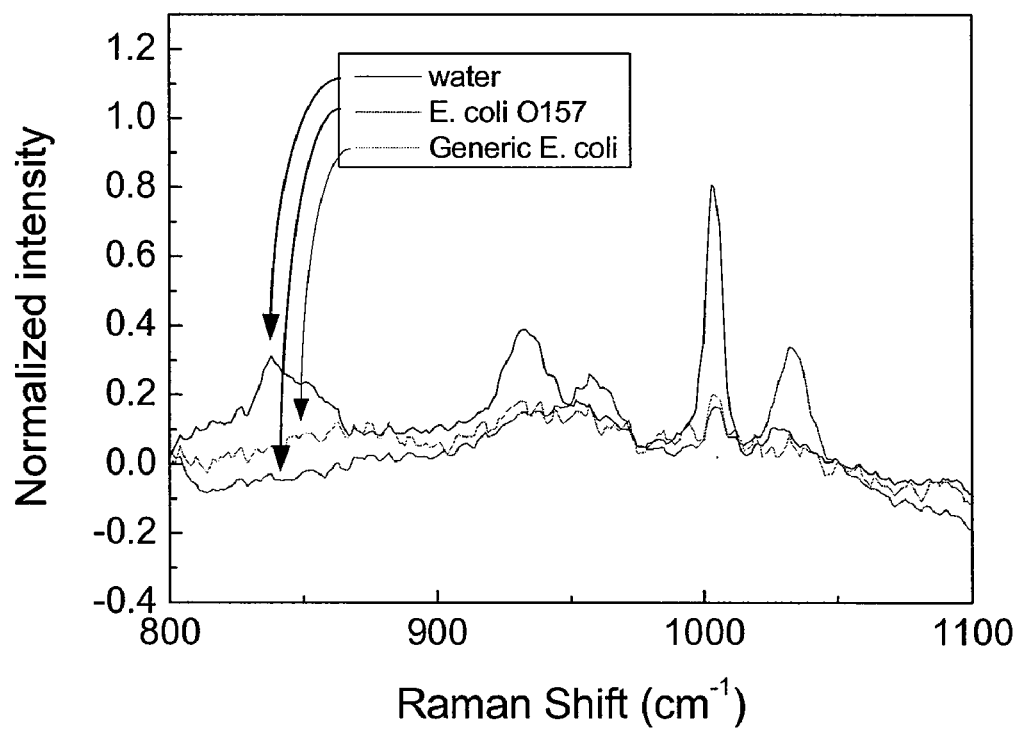
FIG. 12 illustrates the average SERS response for water (control), Generic *E. coli*, and *E. coli* O157:H7 between 800-1100 $cm^{-1}$.
Figure 13:
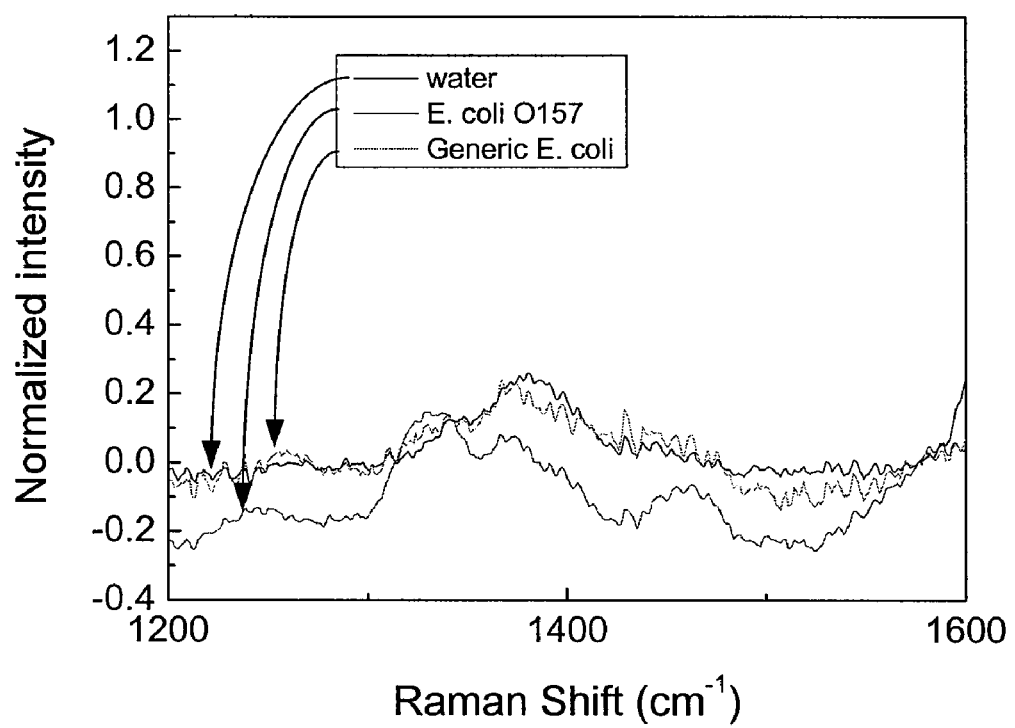
FIG. 13 illustrates the average SERS signal for water (control), Generic *E. coli*, and *E. coli* O157:H7 between 1200-1600 $cm^{-1}$.

The SERS spectra of Generic *E. coli* is characterized by strong bands due to nucleic acid bases at 732 $cm^{-1}$ (adenine), and 1367 $cm^{-1}$ (guanine)[12]. In the SERS spectra for *E. coli* O157, the major peaks are present at 733 $cm^{-1}$ (adenine), 957 $cm^{-1}$ (quanine), 1032 $cm^{-1}$ (Phe) and 1331 $cm^{-1}$ (guannine). A significant characteristic of the SERS spectra is the relative intensity of the bands associated with the nucleic acids indicating direct binding to the Ag substrate. The band at around 733 $cm^{-1}$ was observed in both *E. coli* samples. The strong band at around 733 $cm^{-1}$ has been assigned to denatured DNA caused by its interaction with the Ag SERS substrate. The other prominent peaks around 957 $cm^{-1}$, 1032 $cm^{-1}$, and 1330 $cm^{-1}$ from *E. coli* O157 appeared to be less pronounced in the generic *E. coli* sample. This is illustrated by the spectra in FIG. 11. Each spectrum displayed in FIG. 11 is an average of 6 spectra. Though, both *E. coli* samples share similar characteristic peaks, the relative band widths and intensities of these peaks in the spectra are quite different. These could be due to a difference in the nature of binding of surface proteins of particular bacteria on the SERS substrate. This effect can be observed in the spectral regions between 800-1100 $cm^{-1}$, and again between 1200-1600 $cm^{-1}$, which show intensity difference as well as frequency shifts in the spectra for both bacterial samples. FIGS. 12 and 13 highlight regions within the spectra where differences are apparent. For example, both of the control and Generic *E. coli*, can be differentiated from the *E. coli* O157:H7 samples based on the ratio of peak intensities for the 957 $cm^{-1}$, 1030 $cm^{-1}$ and 1330 $cm^{-1}$ bands.

Conclusions

There is a crucial need for the development of a rapid, sensitive test for the detection of *Escherichia coli* infections and the classification of *Escherichia coli* strains for epidemiological, food safety, and bioterrorism purposes. In the present embodiment, a SERS-based biosensor has been developed and applied to the rapid detection and differentiation of individual *Escherichia coli* strains. Furthermore, the OAD fabrication method has been shown to be capable of economically producing robust, reproducible biosensing SERS substrates which provide extremely high enhancement factors. In the present example, SERS technology correctly distinguished between Generic *E. coli* and *E. coli* O157:H7. This example demonstrates the power of SERS to differentiate closely related strains of *Escherichia coli* in less than one minute. The speed, specificity and ease of implementation of SERS technique represents a valuable alternative to current bacterial diagnostic tools and provides the possibility of portable pathogen sensor for on-site food inspection.

Example 4

Surface enhanced Raman scattering (SERS) using novel silver nanorod array substrates has been used for the detection of pathogenic bacteria. The substrate consists of a base layer of 500 nm silver film on a glass slide and a layer of silver nanorod array with a length of ~1 µm produced by oblique angle deposition method at a vapor incident angle of 86°. Spectra from whole cell bacteria, Generic *Escherichia coli*, *E. coli* O157:H7, *E. coli* DH 5α, *Staphylococcus aureus*, *S. epidermidis* and *Salmonella Typhimurium*, and bacteria mixtures, have been obtained. This SERS active substrate can detect spectral differences between Gram types, different species, their mixture, and strains. Principal component analysis has been applied to classify the spectra. Viable and nonviable cells have also been examined and significantly reduced SERS responses were observed for nonviable cells. SERS detection of bacteria at the single cell level, excited at low incident laser power (12 µW) and short collection time (10 s), has also been demonstrated. These results indicate that the SERS-active silver nanorod arrays substrate is a potential analytical sensor for rapid identification of microorganisms with a minimum sample preparation.

Introduction

The potential risk for deliberate contamination of the environment, food, and agricultural products has recently increased due to the global war on terrorism, making biosensing an important issue for several federal agencies. The current trend is to decentralize large stationary laboratory facilities such that tests can be performed anywhere and under field conditions. Consequently, the development of portable, rapid and sensitive biosensors with on-the-spot interpretation of results is gaining momentum. From the food safety point of view, real-time microbial detection and source identification are becoming increasingly important due to the growing consumer concerns over food-borne disease outbreaks and economic loss from the outbreaks.

The Centers for Disease Control (CDC) estimated that food-borne diseases cause approximately 76 million illnesses, 325,000 hospitalizations, and 5,000 deaths in the United States each year. Known pathogens account for an estimated 14 million illnesses, 60,000 hospitalizations, and 1,800 deaths. (P. S. Mead, L. Slutsker, V. Dietz, L. F. McCaig, J. S. Bresee, C. Shapiro, P. M. Griffin, and R. V. Tauxe, Emerging infectious diseases. 5, 607 (1999), which is incorporated by reference for the corresponding discussion). The most recent food-borne outbreaks include the *E. coli* O157: H7 contaminated spinach and *Salmonella* outbreak linked to Peter Pan® Peanut butter in 2006.

The conventional culture method recommended by the USDA for detection and identification of foodborne pathogens usually requires three general steps: enrichment, colony isolation, and confirmation. Although conventional culturing is the most sensitive detection methodology available, it is time-consuming and requires extensive manual labor. Other methods including polymerase chain reaction (PCR) (C. R. Newton and A. Graham, PCR, 2nd edn., Bios Scientific, Oxford, (1997), which is incorporated by reference for the corresponding discussion), and antibody-based systems (R. S. Mazenko, F. Reiders and J. D. Brewster, J. Microbiol. Meth. 36, 157 (1999), which is incorporated by reference for the corresponding discussion), have been developed as a diagnostic tool to detect pathogens; however, these approaches have elemental restrictions that limit the use outside of a laboratory. False negative/false positive identification with PCR (C. A. Batt, in Listeria, Listeriosis, and Food Safety, T. Ryser and E. H. Marth, Eds. (Marcel Dekker, New York, 1999), 2nd ed., p. 261, which is incorporated by reference for the corresponding discussion), and the multi-steps, chemical reagents required for immunoassay procedures, thus, these methods are neither fast nor robust enough for field detection.

The research directions for improvement of analytical methods obviously falls on 1) the reduction or elimination of the sample preparation procedure, 2) continual and routine analysis of large numbers of samples with minimum reagent usage and cost, 3) ease to operate under most conditions and 4) short data accumulation time. Alternative approaches that satisfy most of the above requirements are spectroscopic techniques that are specific, noninvasive, nondestructive, and can be performed very rapidly. Similar to infrared (IR) spectroscopy, Raman spectroscopy provides detailed information about the material under investigation, often at the molecular level. Raman spectroscopy has advantages over IR such as less interference from water bands in aqueous samples and selection rules that result in fewer spectral bands and thus simpler spectra. It has been used to obtain highly structured information on bacteria. (W. H. Nelson, R. Manoharan, and J. F. Sperry, Appl. Spectrosc. Rev. 27, 67 (1992); Q. Wu, T. Hamilton, W. H. Nelson, S. Elliott, J. F. Sperry, and M. Wu, Anal. Chem. 73, 3432 (2001), which are incorporated by reference for the corresponding discussion), even at the single bacterial cell level. (T. A. Alexander, P. M. Pellegrion, and J. B. Gillespie, Appl. Spectrosc. 57, 1340 (2003), which is incorporated by reference for the corresponding discussion). Although Raman sensitivity is low in comparison to IR spectroscopy, it can be greatly increased by the surface-enhanced Raman scattering.

The effect of drastically enhanced Raman signals rely on either the adsorption or close proximity of a molecule to a rough metal substrate. (M. Fleischmann, P. J. Hendra, A. J. McQuillan, Chem. Phys. Lett. 26, 163 (1974), which is incorporated by reference for the corresponding discussion). When the analyte is in close proximity to the metal, the energy from the plasmon resonance may be coupled into bonds of the molecule of interest resulting in an enhancement of the Raman signal of several orders of magnitude. (M. Moskovits, Rev. Mod. Phys. 57, 783 (1985); A. Campion, and P. Kambhampati, Chem. Soc. Rev. 4, 241 (1998), which are incorporated by reference for the corresponding discussion). Surface-enhanced Raman spectroscopy (SERS) has been used as an analytical tool to observe trace amounts of chemical and biological molecules due to its capability of giving real-time molecular vibrational information under ambient conditions. In addition to signal enhancement, SERS has a fluorescence-quenching effect for molecules attached to a metal nanostructure. (K. Kneipp, A. S. Haka, H. Kneipp, K. Badizadegan, N. Yoshizawa, C. Boone, K. E. Shafer-Peltier, J. T. Motz, R. R. Dasari, and M. S. Feld, Appl. Spectrosc. 56, 150 (2002), which is incorporated by reference for the corresponding discussion). This is extremely valuable when investigating microorganisms or biological samples, which often exhibit a fluorescence background under excitation in the near-infrared to visible regions.

The morphology of the metallic structure plays a major role in determining the magnitude of signal enhancement and sensitivity of detection. (Z. Q. Tian, B. Ren, and D. Y. Wu, J. Phys. Chem. B 106, 9463 (2002), which is incorporated by reference for the corresponding discussion). Early SERS substrates included a random distribution of roughed features produced by oxidation reduction on a metal electrode (A. A. Stacy and R. P. Van Duyne, Chem. Phys. Lett. 102, 365 (1983), which is incorporated by reference for the corresponding discussion), or evaporation of thin metal film on a flat substrate. (G. J. Kovacs, R. O. Louffy, P. S. Vincett, C. Jennings, and R. Aroca, Langmuir 2, 689 (1986), which is incorporated by reference for the corresponding discussion). Various forms of nanostructures have been explored to enhance SERS effects, for example, rough metallic surfaces by chemical etching (K. T. Carron, X. Gi, and M. L. Lewis, Langmuir 7, 2 (1991), which is incorporated by reference for the corresponding discussion), silver films on $TiO_2$ (L. M. Sudnik, K. L. Norrod, and K. L. Rowlen, Appl. Spectrosc. 50, 422 (1996), which is incorporated by reference for the corresponding discussion), colloidal silver nanoparticles (S. M. Nie, and S. R. Emory, Science 275, 1102 (1997), which is incorporated by reference for the corresponding discussion), silver nanoparticle arrays fabricated by nanosphere lithography (T. R. Jensen, M. D. Malinsky, C. L. Haynes, and R. P. Van Duyne, J. Phys. Chem. B 104, 10549 (2000), which is incorporated by reference for the corresponding discussion), electro-deposition of silver on silver films at high potential (G. Suer, U. Nickel, and S. Schneider, J. Raman Spectrosc. 31, 359 (2000), which is incorporated by reference for the corresponding discussion), and aligned monolayer of silver nanowires. (A. Tao, F. Kim, C. Hess, J. Goldberger, R. R. He, Y. G. Sun, Y. N. Xia, and P. D. Yang, Nano Lett. 3, 1229 (2003), which is incorporated by reference for the corresponding discussion). Among them, silver colloids have been used intensely because of their ability to provide the greatest SERS enhancement, and in some cases, these colloids have proven to be capable of trace component/single-molecule detection. (K. Kneipp, G. Kneipp, I. Itzkan, R. R. Dasari, and M. S Feld, Chem. Rev. 99, 2957 (1999, which is incorporated by reference for the corresponding discussion). Ag colloids have been extensively used for SERS bacteria detection as well. (L. Zeiri, B. V. Bronk, Y. Shabtai, J. Czégé, and S. Efrima, Colloids Surfaces A. 208, 357 (2002); R. M. Jarvis, and R. Goodacre, Anal. Chem. 76, 40 (2004); A. Sengupta, M. L. Laucks, and E. J. Davis, Appl. Spectrosc. 59, 1016 (2005); M. L. Laucks, A. Sengupta, K. Junge, E. J. Davis, and B. D. Swanson, Appl. Spectrosc. 59, 1222 (2005); M. Kahraman, M. M. Yazici, F. Sahin, O. F. Bayrak, and M. Culha, Appl. Spectrosc. 61, 479 (2007); M. Kahraman, M. M. Yazici, F. Sahin, O. F. Bayrak, E. Topcu, and M. Culha, Intern. J. Environ. Anal. Chem. 87, 763 (2007); M. Kahraman, M. M. Yazici, F. Sahin, and M. Culha, Langmuir 24, 894 (2008), which are incorporated by reference for the corresponding discussion). Generally, metal colloidal substrates are prone to reproducibility and stability issues, as colloid particles might vary from batch to batch and tend to aggregate and to precipitate in solutions over time. (L. Zeiri, B. V. Bronk, Y. Shabtai, J. Czégé, and S. Efrima, Colloids Surfaces A. 208, 357 (2002); R. M. Jarvis, and R. Goodacre, Anal. Chem. 76, 40 (2004); A. Sengupta, M. L. Laucks, and E. J. Davis, Appl. Spectrosc. 59, 1016 (2005); M. L. Laucks, A. Sengupta, K. Junge, E. J. Davis, and B. D. Swanson, Appl. Spectrosc. 59, 1222 (2005), which are incorporated by reference for the corresponding discussion). Though improved reproducibility can be achieved by convective assembly of optimum bacteria and silver colloidal suspension on a glass slide attached to a moving stage. (M. Kahraman, M. M. Yazici, F. Sahin, and M. Culha, Langmuir 24, 894 (2008), which is incorporated by reference for the corresponding discussion). Other substrate preparation methods are either expensive or time consuming, and it is not easy to make reproducible substrates of the correct surface morphology to provide maximum SERS enhancements. Without uniformity and good reproducibility of the metal substrates, the attainment of reproducible spectra, and thus reliable detection, remains a major challenge for SERS.

Oblique angle deposition (OAD) is a physical vapor deposition technique that overcomes some of the difficulties and disadvantages of the previously mentioned SERS substrate fabrication methods. This method involves positioning the substrate at a specific angle such that the vapor from the source is incident on the substrate close to the grazing angle. This process results in the preferential growth of nanorods on the substrate in the direction of deposition. The resulting surface morphology can be attributed to the fact that nanostructures are grown from initial metal nucleation sites due to a shadowing effect causing the growth of the nanorod arrays aligned in a specific direction. The major advantages of this technique include: a) control over the size, shape, and density of the nanostructures by varying the deposition conditions such as the incident vapor deposition angle, temperature, and the duration and rate of deposition; b) a wide variety of elements can be used to form these nanostructures as long as the material used can be evaporated; c) any standard physical vapor deposition system equipped with a holder capable of rotation in the polar and azimuthal directions can be utilized. By rotating the substrate at controlled speeds in an azimuthal direction, it is possible to achieve complex and unique nanostructure designs, such as nanorod arrays, nanospring arrays, nanospiral arrays, and multilayer nanostructures. (Y.-P. Zhao, D. X. Ye, G. C. Wang, and T. M. Lu, Proc. SPIE. 5219, 59 (2003), which is incorporated by reference for the corresponding discussion). Silver nanorod arrays substrates prepared by the OAD process have previously been shown to provide SERS enhancement factors of $>10^8$. (S. B. Chaney, S. Shanmukh, R. A. Dluhy, and Y.-P. Zhao, Appl. Phys. Lett. 87, 031908.1 (2005); Y.-P. Zhao, S. B. Chaney, S. Shanmukh, and R. A. Dluhy, J. Phys. Chem. B 110, 3153 (2006); Y. Liu, J. Fan, S. Shanmukh, R. A. Dluhy, and Y.-P. Zhao, Appl. Phys. Lett. 89, 173134 (2006); H. Y. Chu, Y.-J. Liu, Y.-W. Huang, and Y.-P. Zhao, Optics Express 15, 12230 (2007); J. Driskell, S. Shanmukh, Y. Liu, S. Chaney, X.-J. Tang, Y.-P. Zhao, and R. Dluhy, J. Phys. Chem. C 112, 895 (2008), which are incorporated by reference for the corresponding discussion). Very recently, the OAD prepared SERS substrates demonstrated its potential to distinguish between viruses. (S. Shanmukh, L. Jones, J. Driskell, Y.-P. Zhao, R. Dluhy, and R. A. Tripp, Nano Lett. 6, 2630 (2006); S. Shanmukh, L. Jones, Y.-P. Zhao, J. D. Driskell, R. A. Tripp and R. A. Dluhy, Anal. Bioanal. Chem. DOI 10.1007/s00216-008-1851-0 (2008), which are incorporated by reference for the corresponding discussion). The OAD technique offers an easy, straightforward and inexpensive way for the fabrication of silver nanorod arrays for high sensitivity SERS applications. The SERS substrates produced by OAD have the advantages of uniformity and reproducibility.

The overall objective of this study was to evaluate the ability of silver nanorod arrays as a SERS substrate to rapidly detect pathogenic bacteria. We also examined the ability of SERS to differentiate between different bacterial species, bacteria mixture, strains and between viable and nonviable cells based on their characteristic SERS spectra. Finally, we explored the possibility to obtain single cell level Raman spectra on these silver nanorod substrates.

Experimental Methods

Fabrication of Substrates

The SERS active substrates used were silver nanorod arrays fabricated by OAD technique using a custom-designed electron beam/sputtering evaporation (E-beam) system (Torr International, New Windsor, N.Y.) that has been previously described. (S. B. Chaney, S. Shanmukh, R. A. Dluhy, and Y.-P. Zhao, Appl. Phys. Lett. 87, 031908.1 (2005), which is incorporated by reference for the corresponding discussion). Glass microscopic slides (Gold Seal® Catalog No. 3010) were used as the base platform for silver nanorod array deposition. The glass slides were cleaned with Piranha solution (80% sulfuric acid, 20% hydrogen peroxide), and rinsed with DI water. The substrates were then dried with a stream of nitrogen gas before loading into the E-beam system. A base layer of Ti (20 nm) and silver film (500 nm) were first evaporated onto the glass slides at normal angle to the substrate surface at a rate of ~0.1 nm/s and 0.3-0.4 nm/s, respectively. The substrates were then rotated by a computer controlled stepper motor to 86° with respect to the vapor incident direction. Ag nanorods were grown at this oblique angle with a nominal deposition rate of ~0.3 nm/s, and a deposition pressure of $~1\times10^{-6}$ Torr. The film thickness was monitored by a quartz crystal microbalance positioned at normal incidence to the vapor source direction. This deposition conditions resulted in optimal SERS substrates with an average nanorod length of 868±95 nm and the average diameter of 99±29 nm. The average density of the nanorods was approximately 13±0.5 rods/μm² with an average tilting angle of ~73° with respect to the substrate normal. Prior to data collection the substrates were stored in vacuum sealed bags at room temperature to avoid any changes in surface morphology due to temperature or atmospheric humidity.

Bacterial Samples

The following bacteria were used in the analyses: Generic *Escherichia coli* (ATCC 29993), *Escherichia coli* O157:H7 (ATCC 43888), *Staphylococcus aureus* (ATCC 6538) and *Staphylococcus epidermidis* (ATCC 33501) were obtained from American Type Culture Collection (Rockville, Md.). *Salmonella typhimurium* 1925-1 poultry isolate and *E. coli* DH 5α were provided by the Department of Food Science and Technology, The University of Georgia. Bacterial cells were grown in trypticase soy broth (TSB, Difco, Detroit, Mich.) over night at 37° C. with 240 rpm shaking. This growth procedure routinely yielded a stock culture containing ~$10^9$ colony forming units (CFU)/ml at stationary phase. Bacterial populations were determined by the conventional surface plate count method using plate count agar (PCA, Difco). Following incubation, the cultures were washed three times with sterilized deionized (DI) water before re-suspending in DI water. Desired dilutions were made in sterilized DI water. Two different types of mixed cell cultures were prepared by mixing equal amount of *E. coli* O157:H7 ($10^8$ CFU/mL) and *Staphylococcus aureus* ($10^8$ CFU/mL); also equal amount of *E. coli* O157:H7 ($10^8$ CFU/mL) and *Salmonella typhimurium* 1925-1 ($10^8$ CFU/mL).

SERS Measurements

SERS spectra were acquired using a HRC-10HT Raman analyzer system (Enwave Optronics Inc. Irvine, Calif.). (Y. Liu, J. Fan, S. Shanmukh, R. A. Dluhy, and Y.-P. Zhao, Appl. Phys. Lett. 89, 173134 (2006), which is incorporated by reference for the corresponding discussion). This system consists of a diode laser, spectrometer, integrated Raman probe head for both excitation and collection, and separate delivery and collection fibers. The excitation source was a frequency stabilized, narrow linewidth near IR diode laser with a wavelength of 785 nm. The excitation laser beam coupled to a 100 μm fiber was focused onto the substrate through the Raman probe head and was unpolarized at the sample. The focal length of the Raman probe was 6 mm and the diameter of the laser spot was 0.1 mm. The Raman signal from the substrate was collected by the same Raman probe head and was coupled to a 200 μm collection fiber which delivered the signal to the spectrometer equipped with a charge coupled device (CCD) detector. The laser power at the sample varied and was monitored with a power meter (PM 121, Thorlabs Inc., Newton, N.J.). The spectral collection time was 10 s. A 2.0-μL aliquot of intact bacteria sample was applied to the Ag nanorod array substrate and allowed to bind for 1 h at room temperature prior to spectrum acquisition. SERS spectra were collected from multiple spots across the substrate and from multiple substrates. Generally, solution spot sizes were 2 mm in diameter. If the concentrations of a culture solution containing ~$10^8$ CFU/ml, there will be roughly 500 cells on the laser spot.

Data Analysis

Enwave Raman analyzer software (Enware Optronics Inc. Irvine, Calif.) was used for instrument control and data collection. The spectral coverage is from 200 cm⁻¹ to 2400 cm⁻¹ with 785 nm excitation. ASCII data were exported from the Raman analyzer software into Origin software 7.0 version (OriginLab Corporation, Northampton, Mass.) for spectra processing, including plotting, baseline correction, normalization and peak detection.

Principal component analysis (PCA) was carried out by Unscrambler version 9.7 (Camo, AS, Norway). Prior to PCA analysis, each SERS spectrum was smoothed using the Savitsky-Golay method with first derivative, a second order polynomial and nine-point smoothing. Spectra were normalized with respect to the most intense peak. Principal components plots were used to visualize the differences between the spectra of each sample.

Results and Discussion

SERS of Background Media

Figure 14:
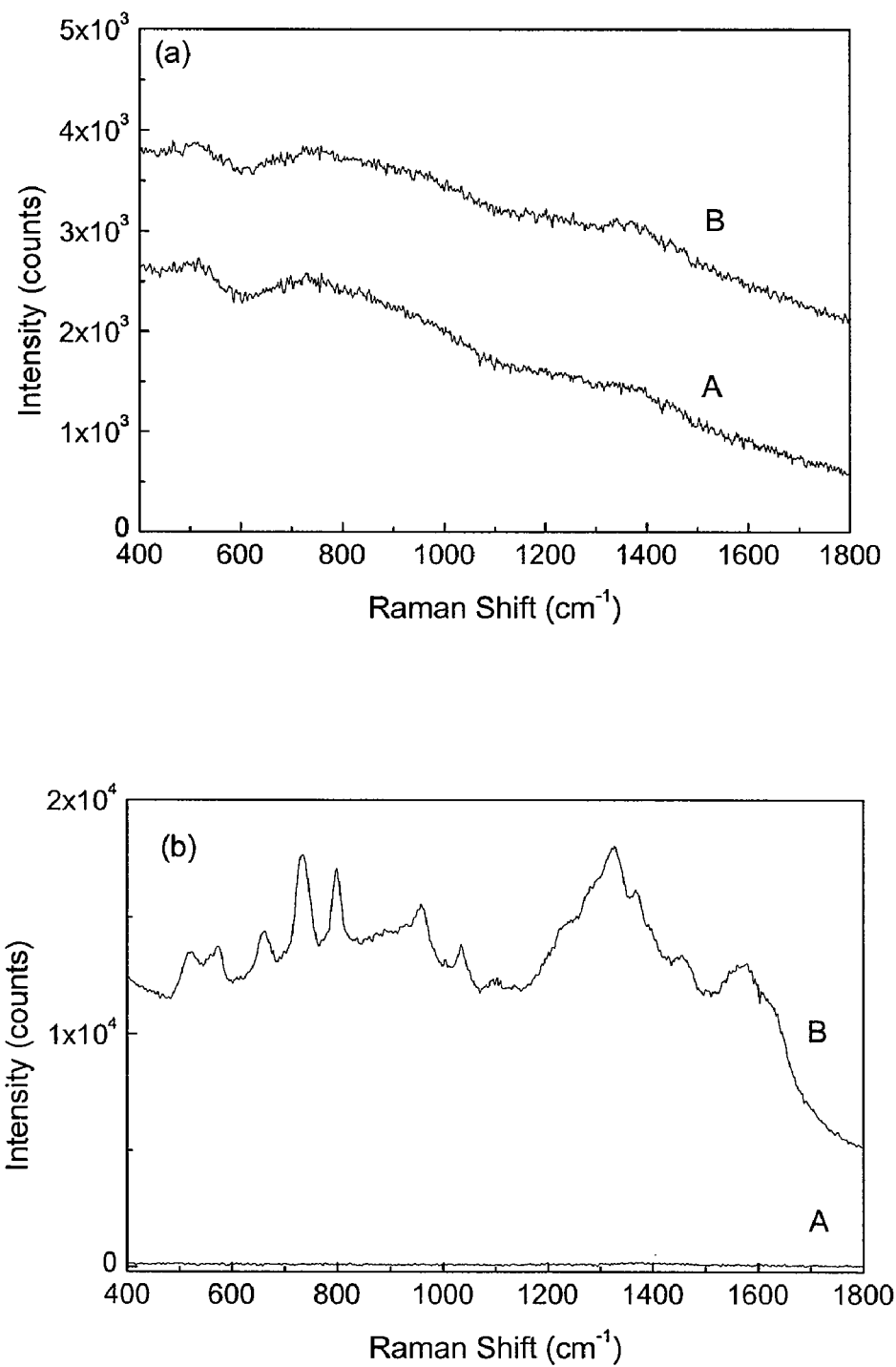
FIG. 14A illustrates Raman spectra of (A) TSB medium; (B) *E. coli* O157 ($10^8$ CFU/ml) in TSB.
FIG. 14B illustrates Raman spectra of (A) DI water; (B) *E. coli* O157 in DI water. Incident laser powers of 69 mW and collection time of 10 s were used to obtain these spectra. Spectra were vertically offset for clarity.

In pathogens, Raman signatures arise predominantly from phenotypic information, including contributions from proteins, nucleic acids (DNA and RNA), lipids, carbohydrates, and endogenous biomolecules. In order to detect and identify pathogens of interest, it is essential to ensure the observed Raman signatures are specific to target microorganisms, but not specific to the environment associated with those microorganisms (e.g., growth media and metabolic products). To examine whether media confound SERS bacterial background signal, Raman spectra directly obtained from trypticase soy broth (TSB) and phosphate buffered saline (PBS), and spectra from *E. coli* inoculated media were compared. A 2.0-μL aliquot of medium solution and 2.0-μL aliquot of *E. coli* inoculated medium samples were applied to the Ag nanorod array substrate and allowed it to dry for 1 h at room temperature prior to spectrum acquisition. FIG. 14A shows the Raman spectra of TSB medium and *E. coli* inoculated TSB. There were no significant spectral differences between TSB and bacteria cells inoculated with TSB. Similarly, there was no significant spectral feature in the Raman spectra of *E. coli* inoculated PBS (figure not shown). The chemical components and/or metabolic byproducts in the media could have interfered or obscured the spectral features of microorganisms. To purify *E. coli* cells, wash steps (in DI water) followed by centrifugation were then incorporated prior to spectra collection. After samples were washed and centrifuged, significant differences in spectral features were readily visible (FIG. 14B). Therefore, it was necessary to incorporate additional separation technique, such as washing and centrifugation, into a bacterial detection and identification procedure based on SERS. Consequently, bacteria purification steps were included in the sample preparation procedures in all our further studies.

SERS Reproducibility

Figure 15:
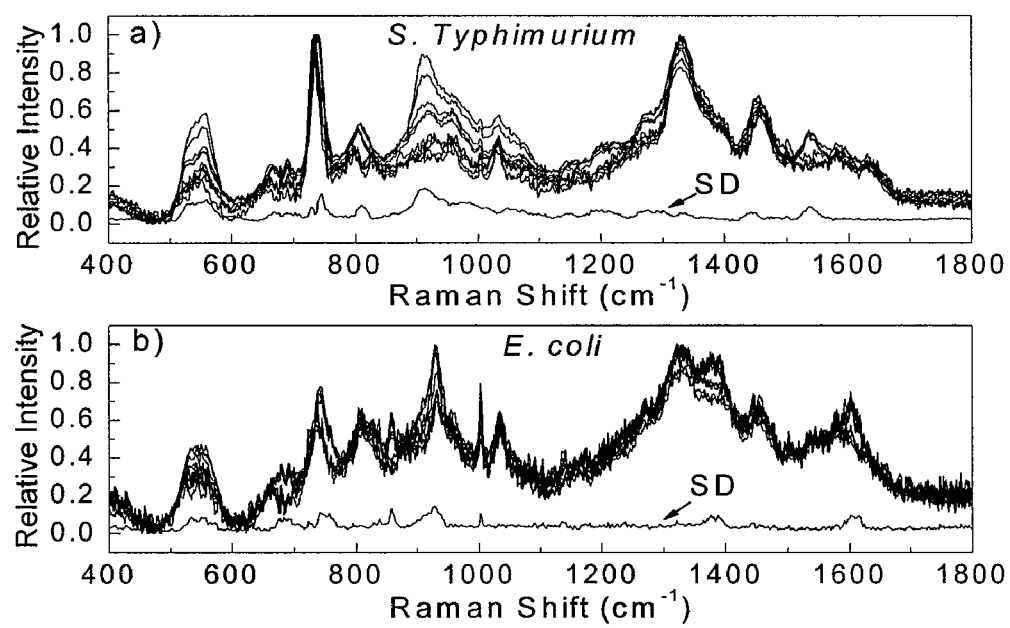
FIGS. 15A through 15B illustrate SERS spectra of *S. typhimurium* (FIG. 15A) and *E. coli* O157:H7 (FIG. 15B) normalized to the peak intensity of the most intense peak are overlapped in order to demonstrate the SERS signal reproducibility from different areas of the same substrate. Spectra were collected from several spots on different substrates. Incident laser powers of 35 mW and collection time of 10 s were used to obtain these spectra. The standard deviation (SD) spectrum for each species is shown at the bottom of each plot.

As mentioned earlier, the morphology of the metallic structure plays a major role in determining the magnitude of signal enhancement and sensitivity of detection. The major obstacle to the widespread use of SERS for analytical applications is to produce sensitive and uniform substrates for reproducible SERS spectra. One way to measure the SERS spectral reproducibility with silver nanorod array substrates is illustrated in FIG. 15. Viable *E. coli* O157:H7 and *S. typhimurium* cells were first purified and re-suspended in DI water before being applied on the silver nanorod array substrates. SERS spectra collected from separate spots on the substrate and from different substrates, were normalized with respect to the most intense band in each spectrum and are displayed in FIG. 15. From the overlaid spectra it is obvious that the spectra of *E. coli* O157:H7 and *S. typhimurium* obtained on the silver nanorod substrates have a high degree of reproducibility. Corresponding standard deviation spectra for these data sets are also displayed in this figure. The relative standard deviation of these spectra for each of these species is ~6% at 735 cm⁻¹ and 1328 cm⁻¹ (maximum signal). The highest deviation for the spectra of these two species is at the band from 500 cm$^{-1}$ to 600 cm$^{-1}$, where over 50% deviation is observed. This high deviation at lower Raman wavenumber shift could be due to instrumental limitations. For *S. typhimurium*, the band at 910 cm$^{-1}$ also displays ~30% deviation. Other than these two particular bands, our results demonstrate a high degree of reproducibility achieved with these SERS substrates. The small variation observed between individual spectra of a particular species could be attributed to the slight inhomogeneous surface morphology, or the statistical distribution of the bacteria in the detection spot. Some spectral differences may result from the molecular orientation of the components of the bacteria on the substrate surface and from the molecular interaction with metal surfaces. In addition, FIG. 15 also shows that the spectral features of *E. coli* O157:H7 is different from those of *S. typhimurium*, which demonstrates the ability of SERS to differentiate different species of bacteria.

SERS of Bacteria: Species Specificity

Figure 16:
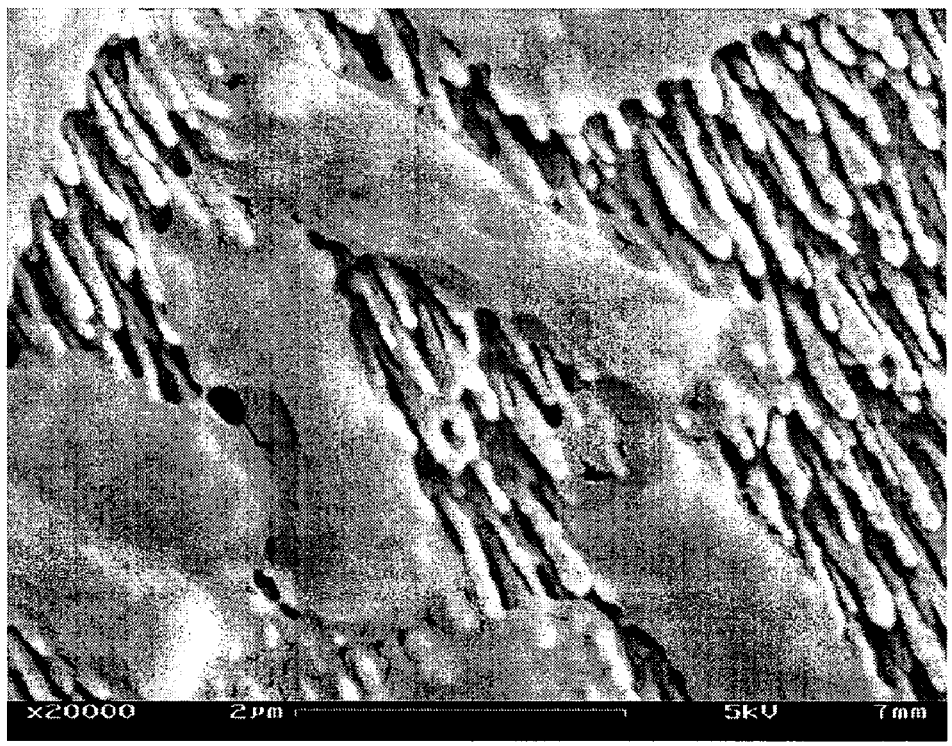
FIG. 16 is a digital image that illustrates a SEM image of *E. coli* bacteria on a silver nanorod array substrate. The scale bar represents 2 µm. Since the cells did not appear to be lysed, the shifts observed in the SERS spectra are a product of cell wall biochemistry or other chemical components external to the cell.
Figure 17:
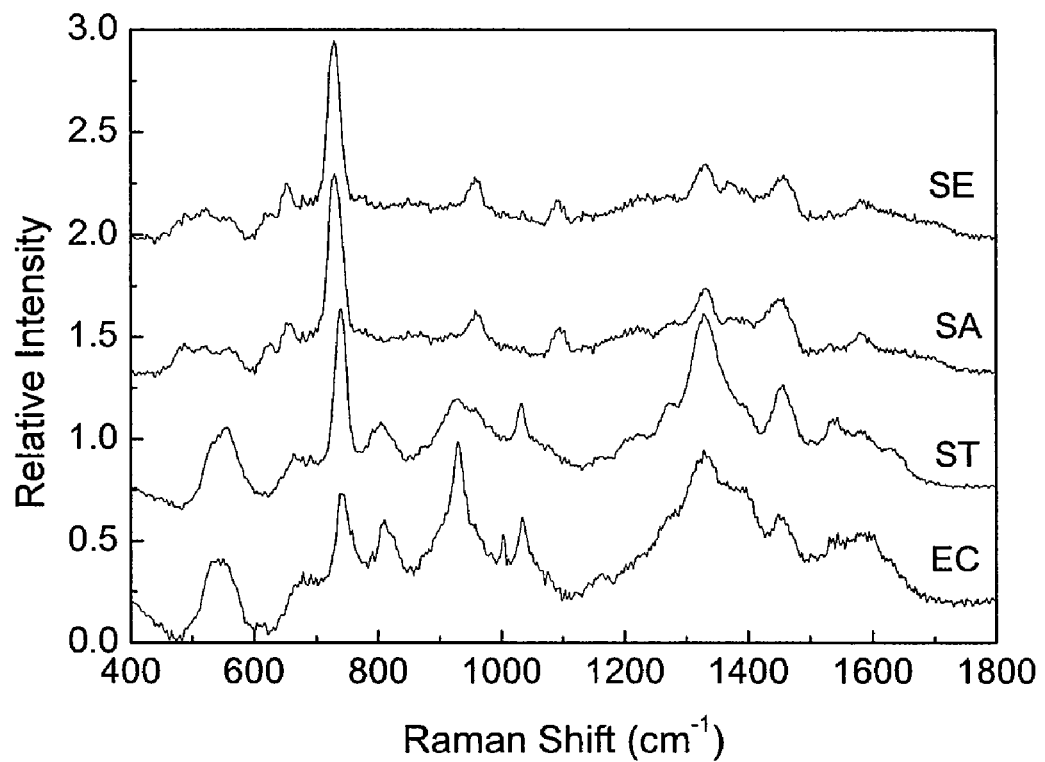
FIG. 17 illustrates average SERS spectra of four bacterial species obtained on silver nanorod array substrates. EC=*E. coli* O157:H7; ST=*Salmonella typhimurium*; SA=*Staphylococcus aureus* and SE=*Staphylococcus epidermidis*. Incident laser powers of 24 mW and collection time of 10 s were used to obtain these spectra. Spectra were offset vertically for display clarity.

To further determine the capability of SERS to distinguish between different bacteria species, SERS spectra of four bacterial species, Gram-negative *E. coli* O157:H7 and *S. typhimurium*, Gram-positive *S. aureus* and *S. epidermidis* were obtained. All four bacterial species reported here were intact and viable cells before being deposited on the silver nanorod array substrates. FIG. 16 shows an SEM image of *E. coli* O157:H7 on a substrate. It appears that the bacteria cell is significantly larger than the Ag nanorod and each cell covers 10-30 Ag nanorods. Since the cells did not appear to be lysed, and the SERS is a short range effect (T. Vo-Dinh, Trends in Analytical Chemistry 17, 557 (1998), which is incorporated by reference for the corresponding discussion), the Raman shifts observed in the SERS spectra of the bacteria on Ag nanorod substrates are a product of cell wall biochemistry or other chemical components external to the cell. FIG. 17 plots the average SERS spectra of the four species of bacteria in the 400-1800 cm$^{-1}$ region. To remove spectral discrepancies caused by the substrates, each SERS spectrum was normalized with respect to its most intense peak. These spectra were acquired with ~24 mW of incident laser power and 10 s collection time. These results demonstrate that SERS spectra of bacteria with good signal-to-noise ratio spectra can be readily obtained when cells are absorbed on these silver nanorod array substrates and excited by low laser power at 785 nm. The SERS spectra in FIG. 17 were arranged from top to bottom according to their Gram stain classifications, with bacteria belonging to the same Gram type adjacent to each other. Spectral differences ascribed to different Gram types, such as *E. coli* O157:H7, *S. typhimurium* and *S. aureus*, could be discerned by naked eyes, while spectral differences attributed to closely related species are not immediately striking. For example, SERS spectra of *S. aureus* and *S. epidermidis* exhibit clear similarities, though, on closer inspection, there are subtle quantitative differences in their relative intensities. Qualitatively, numbers of major spectral bands, such as bands at ~735, 1330 and 1450 cm$^1$, are found to be common to all these species, although their relative intensities vary. There are also differences, such as bands at ~550 and ~1030 cm$^{-1}$ significant to *E. coli* O157:H7 and *S. typhimurium*, a band at ~1090 cm$^{-1}$ unique for *S. aureus* and *S. epidermidis*, and differences among the spectra in the 800-1100 cm$^{-1}$ region.

At this point, molecular level interpretation of SERS vibrational features has not been universally established yet, but based on the spectral position; we can make some general statements. In bacteria detection, Raman signatures from proteins, phospholipids, nucleic acids, and carbohydrates are anticipated to contribute to the spectra. The ubiquitous strong SERS band at ~735 cm$^{-1}$ and the broad band at ~1330 cm$^{-1}$, for example, have been attributed to the nucleic acid base adenine in previous SERS studies of nucleic acid components and bacterial components. (K. Kneipp, and J. Flemming, J. Mol. Struct. 145, 173 (1986); L. Zeiri, B. V. Bronk, Y. Shabtai, J. Eichler, and S. Efrima, Appl. Spectrosc. 58, 33 (2004), which are incorporated by reference for the corresponding discussion). As demonstrated by FIG. 16, the cells are not broken apart and only lie on top of the Ag nanorods, the SERS spectrum is most sensitive to the outer bacterial cell layer. Molecules and functional groups that are in the immediate proximity of the metal surface should predominate in a SERS measurement. Thus, in SERS band assignment, molecular components of the cell wall and membrane should favor over nucleic acids that are located internally. Therefore, the ~735 cm$^{-1}$ cannot be straightforwardly explained by the presence of adenine containing compounds on the outer surface of bacterial cells. Another possibility is the secretion of small molecules by the cell. On the other hand, phospholipids and polysaccharides also have bands in this region and are significant components of cell membrane structures. (K. J. Rothschild, J. R. Andrew, W. J. DeGrip, and H. E. Stanely, Science 191, 1176 (1976), which is incorporated by reference for the corresponding discussion). Another Raman signature common to all these four species at ~1450 cm$^{-1}$ can be attributed to the CH$_2$ deformation mode of proteins. (E. Podstawka, Y. Ozaki, and L. M. Proniewicz, Appl. Spectrosc. 58, 570 (2004), which is incorporated by reference for the corresponding discussion). To match some of the other bands to characteristic functional groups, the broad band at ~550 cm$^{-1}$ observed in both the spectra of *E. coli* O157:H7 and *S. typhimurium* can be assigned to carbohydrate. (K. C. Schuster, E. Urlaub, and J. R. Gapes, J. Microbiol. Methods 42, 29 (2000), which is incorporated by reference for the corresponding discussion). The strong band at ~930 cm$^{-1}$ may have some contributions from the background signal of the substrate, though this band had also been assigned to C-C stretching modes in proteins. (J. S. Suh, and M. Moskovits, J. Am. Chem. Soc. 108, 4711 (1986), which is incorporated by reference for the corresponding discussion). The small band at 1030 cm$^{-1}$ can be attributed to carbohydrate. (K. C. Schuster, E. Urlaub, and J. R. Gapes, J. Microbiol. Methods 42, 29 (2000), which is incorporated by reference for the corresponding discussion). The band at ~1090 cm$^{-1}$ is unique for *S. aureus* and *S. epidermidis*, and is associated with protein. (E. Podstawka, Y. Ozaki, and L. M. Proniewicz, Appl. Spectrosc. 58, 570 (2004), which is incorporated by reference for the corresponding discussion). Vibrational bands in the 930-1130 cm$^{-1}$ region have also been previously assigned to membrane phospholipids and proteins. (K. J. Rothschild, J. R. Andrew, W. J. DeGrip, and H. E. Stanely, Science 191, 1176 (1976), which is incorporated by reference for the corresponding discussion). The band at ~1600 cm$^{-1}$ seen in all the spectra is most likely from the substrate. It should be noted that blank Ag nanorod SERS substrates produced by OAD method normally have background contributions that have previously been attributed to carbonaceous material adsorbing onto the substrate during the fabrication of the SERS substrate and storage in ambient conditions. (J. Driskell, S. Shanmukh, Y. Liu, S. Chaney, X.-J. Tang, Y.-P. Zhao, and R. Dluhy, J. Phys. Chem. C 112, 895 (2008); C. E. Taylor, S. D. Garvey, and J. E. Pemberton, Anal. Chem. 68, 2401 (1996), which are incorporated by reference for the corresponding discussion). Such background signals are commonly encountered in SERS, and they were found to remain unchanged throughout the studies and exposure to laser radiation did not affect their position.

Considering the more evident difference in their cell envelope biochemistry for Gram negative versus Gram positive bacteria, the assumption was that the SERS spectra for these two types of bacteria would be quite different. This does not seem to be the case from our observation; the fact that all the SERS spectra share several similar key bands suggests the possibility that SERS comes from a small number of SERS-promoting molecules which are prevalent in all cell surfaces. Zeiri, et al. reported that spectra measured for four different bacterial strains, representing both Gram-negative and Gram-positive bacteria, were essentially identical. (L. Zeiri, B. V. Bronk, Y. Shabtai, J. Czege, and S. Efrima, Colloids Surfaces A. 208, 357 (2002), which is incorporated by reference for the corresponding discussion). The authors suggested that silver colloid particles bind only to certain specific groups on the bacterial cell wall (e.g., flavins). The cell walls of both Gram positive and negative bacteria contain a ubiquitous component called peptidoglycan, which is a polymer of disaccharide (glycan) cross-linked by short chains of amino acids. The glycan backbone is made up of alternating molecules of N-acetylglucosamine (NAG) and N-acetylmuramic acid (NAM). There has been report of SERS spectra of NAG showing an intense peak at ~730 $cm^{-1}$ (R. M. Jarvis, and R. Goodacre, Anal. Chem. 76, 40 (2004), which is incorporated by reference for the corresponding discussion), which could explain the ever-present peak at ~735 $cm^{-1}$ in our spectra of both Gram negative and positive bacteria. Though there is potential to obtain chemical information from these SERS spectra, they are difficult to interpret. Although resources for standard Raman spectra of biological materials are slowly becoming available and can be useful, it is not always the case that peaks expressed in a Raman spectrum will also be observed in the SERS spectrum of the same sample. Obviously in a complex multi-component system such as a bacterial cell, there could be any number of SERS-active vibrational modes present thus, peak attributions should remain cautious and tentative, unless composition of the cells and their model compounds are thoroughly examined and independent references are employed. Nevertheless, the combination of differences and similarities among the spectra allow the potential use of SERS to distinguish bacterial species.

Classification of Bacteria Species

Visual inspection of spectra with great similarity for classification could be trying, subjective and unrealistic. To classify and identify microorganisms based on vibrational spectra, it is not necessary to identify all band intensities and frequencies in a spectrum and assign them to specific molecular compounds. Spectra can be evaluated as spectroscopic fingerprints of the samples. (J. J. Laserna, Anal. Chim. Acta. 283, 607 (1993); A. E. Grow, L. W. Laurie, J. L. Claycomb, and P. A. Thompson, J. Microbiol. Methods, 53, 221 (2003), which are incorporated by reference for the corresponding discussion). Principal component analysis (PCA) can highlight the minute spectral differences and can objectively differentiate between similar spectra. PCA is a method of recasting the multi-dimensional data onto a new set of axes or orthogonal basis vectors that are typically called principal components (PC). The PC containing the greatest variance is labeled PC 1, while the axis containing the second most variance is labeled PC 2 and so on. PCs model the most statistically significant variations in the dataset and are primarily used to reduce the dimensionality of the sample matrix prior to the use of clustering methods. To explore the data and identify individual groups based on differences in the SERS spectra, PCA was employed to 'cluster' samples into groups. There are few reports where PCA method was employed to analyze SERS spectra of bacteria. (R. M. Jarvis, and R. Goodacre, Anal. Chem. 76, 40 (2004); R. M. Jarvis, A. Brooker, and R. Goodacre, Anal Chem 76, 5198 (2004); W. F. Pearman, and A. W. Fountain, Appl. Spectrosc. 60, 356 (2006), which are incorporated by reference for the corresponding discussion). Application of chemometrics to SERS has been limited due to the irreproducibility limitations of some SERS substrates. As we have demonstrated in FIG. 15, the SERS substrate produced by OAD method can produce reproducible SERS spectra of bacteria, which makes the chemometrics method applicable to classify the bacteria species from SERS data. Here we apply the PCA method to classify bacteria based on data shown in FIG. 17.

Figure 18:
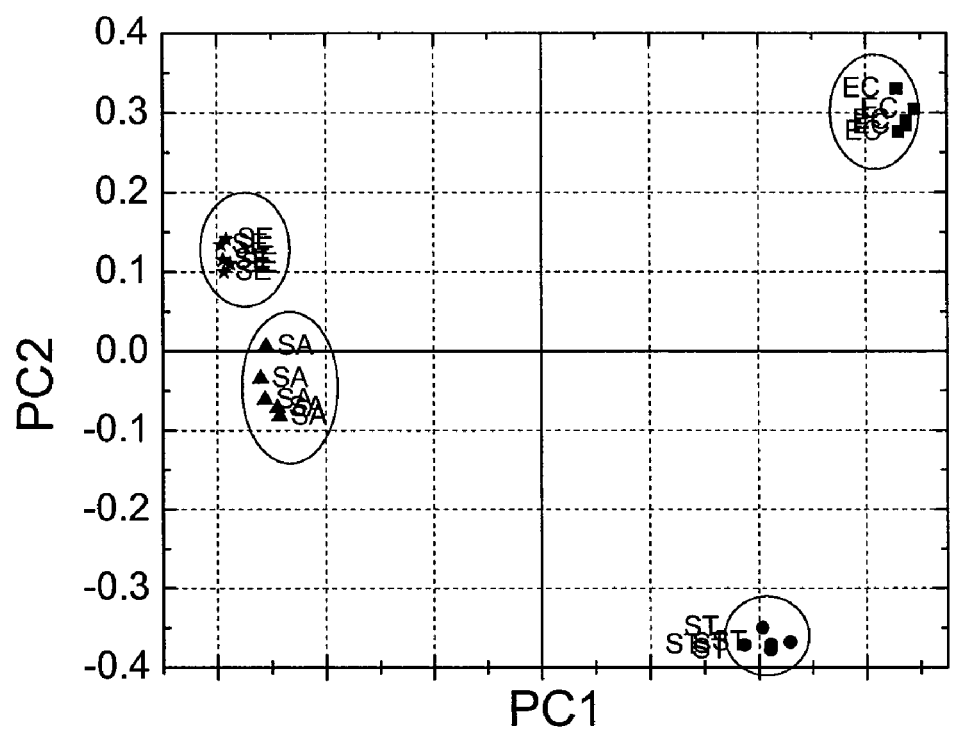
FIG. 18 illustrates PCA scores plot of *E. coli* O157:H7 (EC). *Salmonella typhimurium* (ST), *Staphylococcus aureus* (SA), and *Staphylococcus epidermidis* (SE) pure cell samples. The PCA model was constructed using the spectral range from 400-1800 $cm^{-1}$.

FIG. 18 shows the PCA analysis performed using the SERS spectral data from the four pure bacteria samples, *E. coli* O157:H7 (EC), *S. typhimurium* (ST), *S. aureus* (SA) and *S. epidermidis* (SE) in the 400-1800 $cm^{-1}$ range. Four different clusters appear in the PCA plot, and each cluster corresponds to individual bacteria specie: The *E. coli* O157:H7 has positive PC1 and PC2 scores, while the *S. typhimurium* has a positive PC1 score but a negative PC2 score. The *S. aureus* has negative PC1 and PC2 scores (except one data point), and the *S. epidermidis* has a negative PC1 score and a positive PC2 score. In previous colloidal SERS study of bacteria, Jarvis et al. indicated two separate clusters in PCA plot demonstrate good spectral reproducibility and potential for classification of *B. subtilis* and *E. coli*. (R. M. Jarvis, A. Brooker, and R. Goodacre, Anal Chem 76, 5198 (2004), which is incorporated by reference for the corresponding discussion). Although similar to those reported by Jarvis, et al., spectra belonging to different Gram classes lie in different regions, the positive PC1 scores for *E. coli* (Gram negative) and negative PC1 scores for Gram positive bacteria, individual species spectra appear to cluster tighter together in our PCA plot (FIG. 18). This indicates the high degree of spot-to-spot reproducibility of our spectra and that the OAD fabricated substrate can be used to distinguish different bacteria species through PCA process, even though some of the spectra visually look similar.

SERS of Bacteria and Bacteria Mixture

Figure 19:
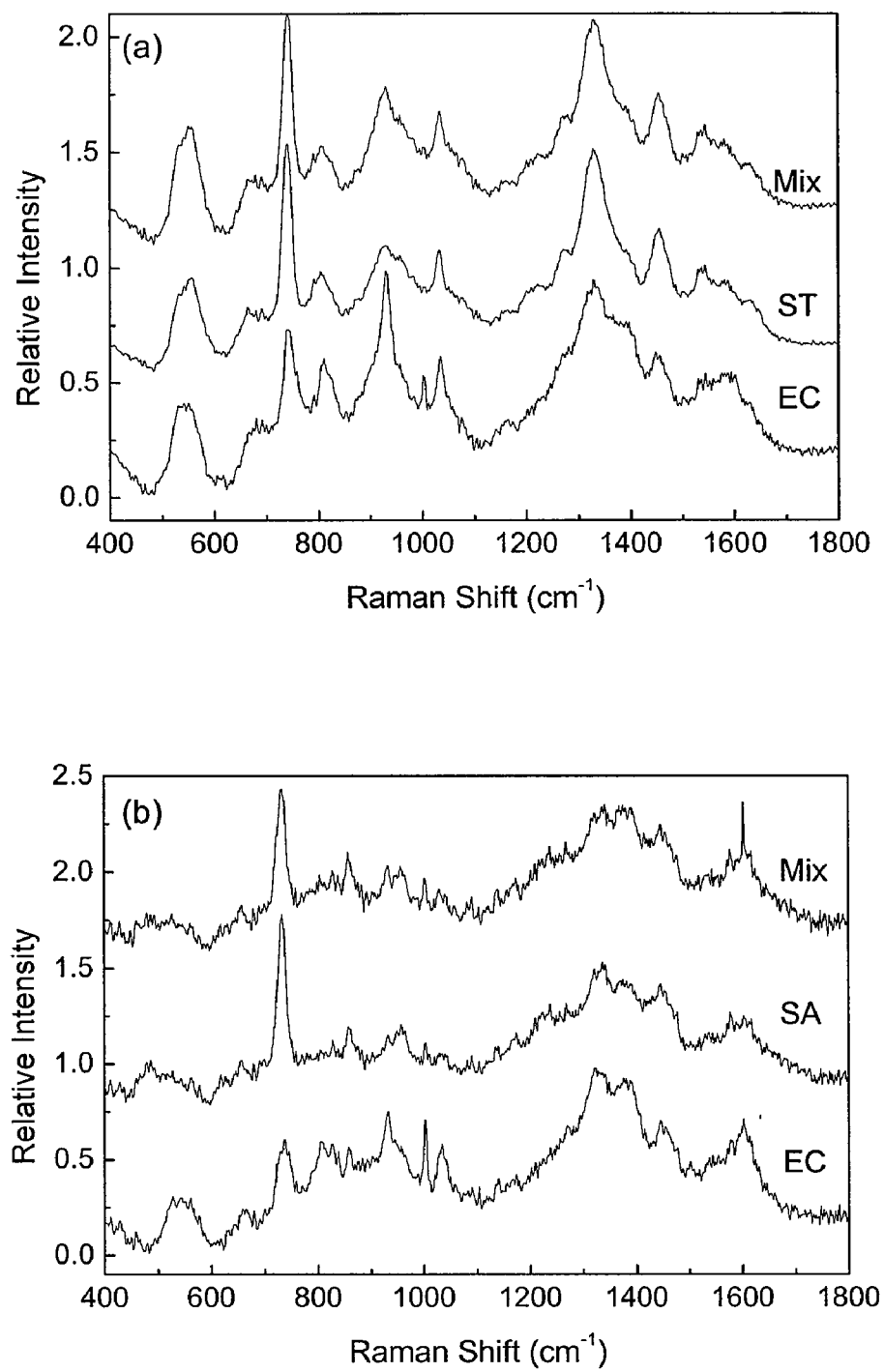
FIGS. 19A through 19B illustrate typical SERS spectra of two bacterial species and its mix culture obtained on silver nanorod array substrates.

To assess the ability of SERS to distinguish Raman signatures of a pure cell sample from a mixed culture, two different types of mixed cell cultures were evaluated. First, the mixture of closely related species that belongs to the Gram negative class, *E. coli* O157:H7 and *S. typhimurium*; second, the mixture of Gram positive and negative species, *S. aureus* and *E. coli* O157:H7. The average SERS spectra of pure cell samples and the mixed culture containing *E. coli* O157:H7 and *S. typhimurium* are shown in FIG. 19A. The similarities among the spectra of the pure cultures of *E. coli* O157:H7 and *S. typhimurium* to the mixture are not surprising since both species share similar chemical compositions and cellular structure, as discussed previously. The main bands in the spectra of these samples may be associated with carbohydrate (~550, 1030 $cm^{-1}$) and protein (~1450 $cm^{-1}$). (K. C. Schuster, E. Urlaub, and J. R. Gapes, J. Microbiol. Methods 42, 29 (2000), which is incorporated by reference for the corresponding discussion). The strong SERS band at ~735 $cm^{-1}$ and the broad band at ~1330 $cm^{-1}$ have been attributed to the nucleic acid base adenine. (K. Kneipp, and J. Flemming, J. Mol. Struct. 145, 173 (1986); L. Zeiri, B. V. Bronk, Y. Shabtai, J. Eichler, and S. Efrima, Appl. Spectrosc. 58, 33 (2004); E. Podstawka, Y. Ozaki, and L. M. Proniewicz, Appl. Spectrosc. 58, 570 (2004), which are incorporated by reference for the corresponding discussion). However, polysaccharides, protein and phospholipids also have been assigned to these bands and are significant components of cell membrane structures. (R. M. Jarvis, and R. Goodacre, Anal. Chem. 76, 40 (2004); K. J. Rothschild, J. R. Andrew, W. J. DeGrip, and H. E. Stanely, Science 191, 1176 (1976), which are incorporated by reference for the corresponding discussion). Despite the similarities in these spectra, some differences can still be observed upon closer inspection. The average SERS spectra of the mixture containing *S. aureus* and *E. coli* O157:H7 and SERS spectra of the respective pure culture are shown in FIG. 19B. Since *S. aureus* and *E. coli* O157:H7 belong to different Gram types and have evident differences in the cell envelope components, we expected to have more pronounced spectral variation. Based on our data, this does not seem to be the case. Though there are visible spectral differences in terms of ratio of band intensities between *S. aureus* and *E. coli* O157:H7, the main bands (~550, 735, 1030, 1330, and 1450 $cm^{-1}$) appear common to both pure cell samples and the mixture sample.

Figure 20:
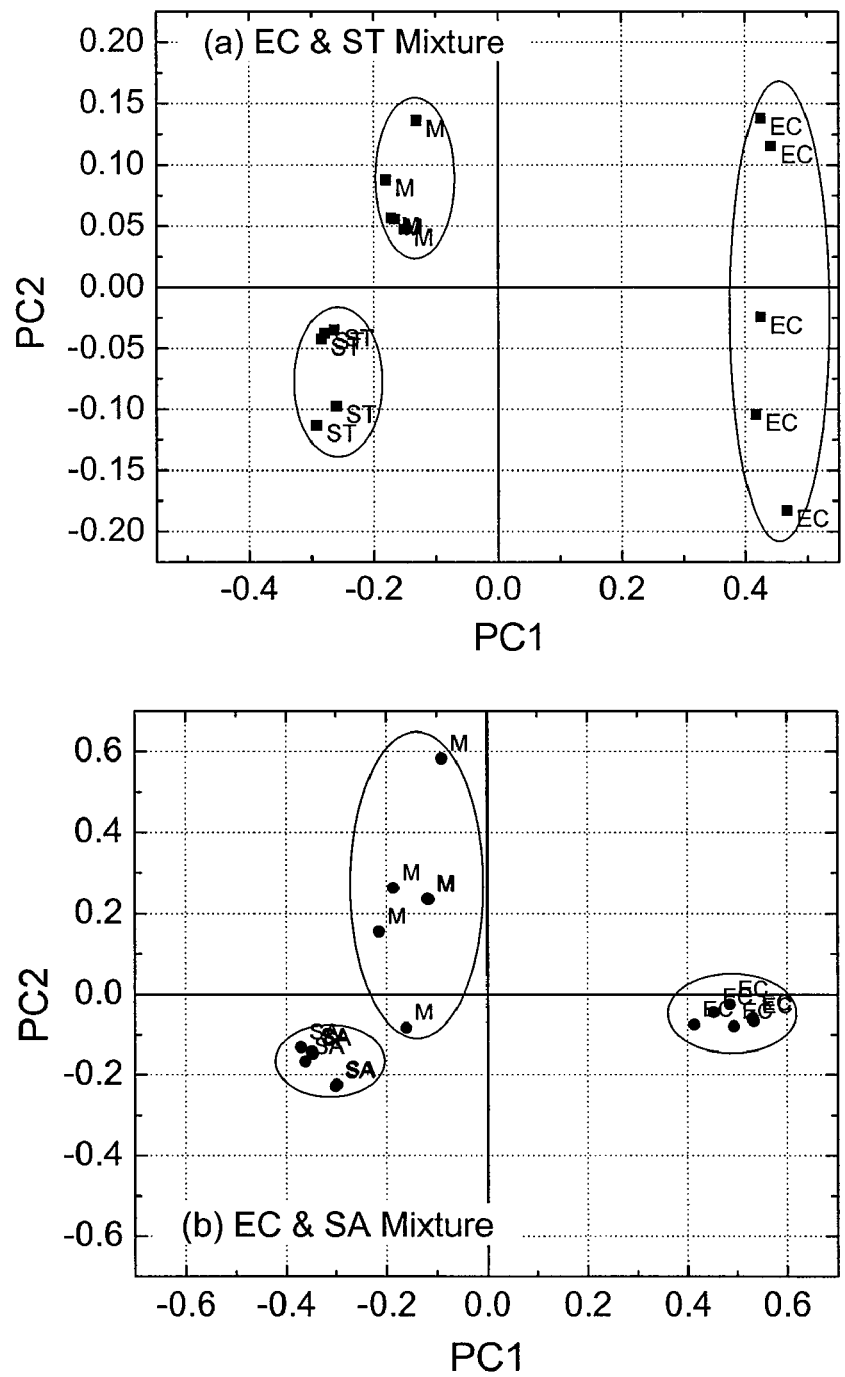
FIG. 20A illustrates PCA scores plot of *E. coli* O157:H7 (EC), *S. typhimurium* (ST) pure cell samples and their mixed cell samples (M).
FIG. 20B illustrates PCA scores plot of *E. coli* O157:H7 (EC); *S. aureus* (SA) pure cell samples and their mixed cell samples (M). The PCA model was constructed using the spectral range from 400-1800 $cm^{-1}$.

In order to classify the bacteria and their mixture, PCA analysis has been carried out. FIG. 20A shows the PCA analysis performed using spectral data from two pure cell samples and their mixtures of the same Gram type, *E. coli* O157:H7 and *S. typhimurium*, in the 400-1800 $cm^{-1}$ range. This score plot indicates that three separated clusters for *E. coli* O157:H7, *S. typhimurium*, and their mixture, respectively. One of the clusters refers to SERS spectra of *E. coli* O157:H7 (coded EC), is clearly away from the other clusters. Another cluster associated with spectra of *S. typhimurium* (coded ST) is located closer to the third cluster (spectra of mix cell samples, coded M). The cluster for *E. coli* O157:H7 has a positive score for PC1, but spread much widely in PC2 axis. The cluster for *S. typhimurium* has a negative PC1 score and a negative PC2 score, while the cluster for the mixture has a negative PC1 score but a positive PC2 score.

FIG. 20B shows the PCA analysis performed using spectral data from two pure cell samples of different Gram types, E. coli O157:H7 and *S. aureus*, and their mixture. This score plot also indicates that three separated clusters for *E. coli* O157:H7, *S. aureus*, and their mixture, respectively. However, unlike the plot in FIG. 20A, the data in the cluster for *E. coli* O157:H7 are much tighter, while the cluster for *S. aureus* is not as well separated from the data for mixture as those for *S. typhimurium* shown in FIG. 20A. Nevertheless, the clusters also follow the general rule as shown in FIG. 20A: the cluster for *E. coli* O157:H7 has a positive PC1 score; the cluster for *S. aureus* has a negative PC1 score and a negative PC2 score, and the cluster for the mixture has a negative PC1 score and a positive PC2 score (except for one data point). This result indicates that one can clearly classify *E. coli* O157:H7, *S. aureus*, and their mixture using SERS spectra obtained on Ag nanorod substrates through the PCA method. However, PCA could not identify the individual spectral characteristics of single cell species in a spectral set of a mixture. This objective can be achieved by forming standard sets of each pure cell samples and testing the individual spectrum from the mixture sample against these standard calibration sets. But for cells with similar SERS spectra, the fingerprint method may not work effectively. A more sophisticated data analysis method should be developed.

Strain Specificity

Figure 21:
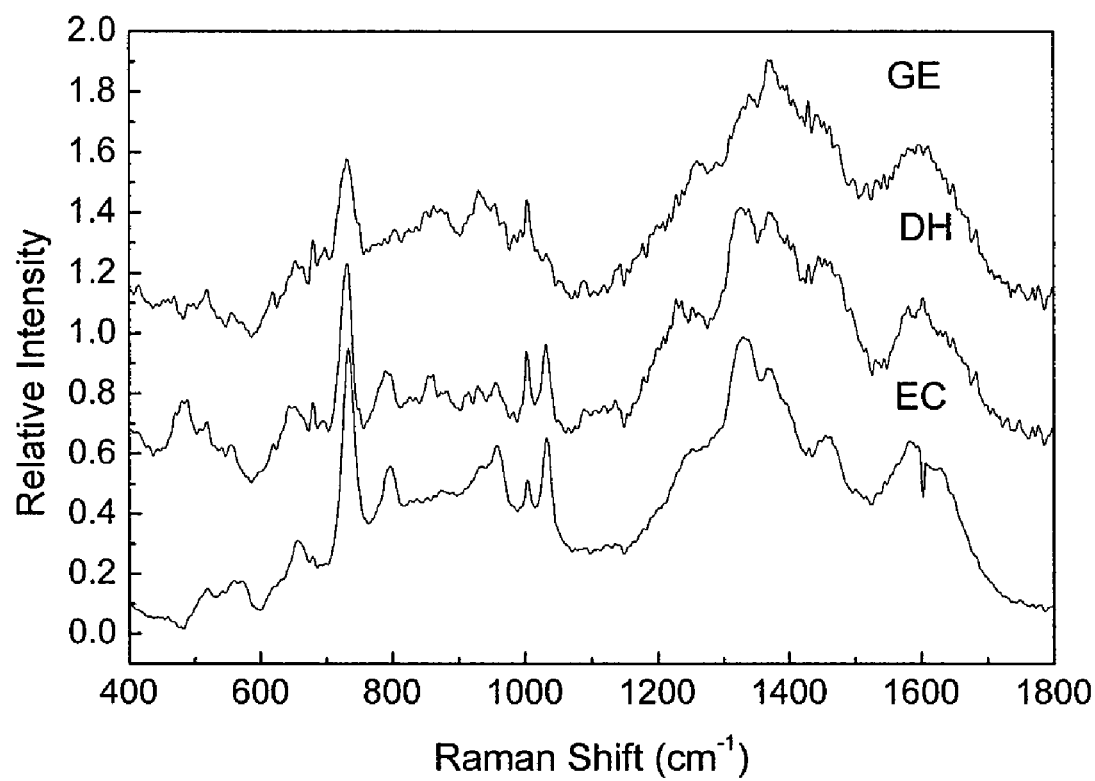
FIG. 21 illustrates average SERS spectra of the *E. coli* strains. EC=*E. coli* O157:H7; DH=*E. coli* DH 5α; GE=generic *E. coli*. Incident laser powers of 69 mW and collection time of 10 s were used to obtain these spectra. Spectra collected from multiple spots for each strain were baseline corrected and normalized to the most intense band. Spectra were offset vertically for display clarity.

Since SERS could detect and differentiate among different species, it was important to determine if different strains of the same species could be distinguished by SERS on these silver nanorod substrates. *E. coli* O157:H7, generic *E. coli* and *E. coli* DH 5α were analyzed to explore this possibility. SERS analysis of these three strains of *E. coli* and their respective spectra are displayed in FIG. 21. Based on the finding for *E. coli* O157:H7 (FIG. 17), the observation was that primary SERS bands should attribute to surface protein, membrane phospholipids and polysaccharides. The sharp band at ~735 $cm^{-1}$ and the broad bands at 1330 $cm^{-1}$ and ~1450 $cm^{-1}$ in the spectra are common to all three strains. Although, the closely related chemical composition and structure of the *E. coli* strains would give rise to very similar SERS spectra, minor but noticeable differences were expected in the spectra for different *E. coli* strains. Each spectrum displayed in FIG. 21 was an average of 6 spectra. While all these *E. coli* samples shared some similar characteristic peaks, the relative band widths and intensities of these peaks in the spectra are somewhat different. This effect can be observed in the spectral region of 400-800 $cm^{-1}$, and again in the 800-1100 $cm^{-1}$ region, which shows intensity differences as well as frequency shifts in the spectra among different strains. Although the basis of most of these bands can be traced from one spectrum to the next, the overall vibrational signature of each strain is unique, allowing fingerprinting potential for bacterial strain identification purposes.

Figure 22:
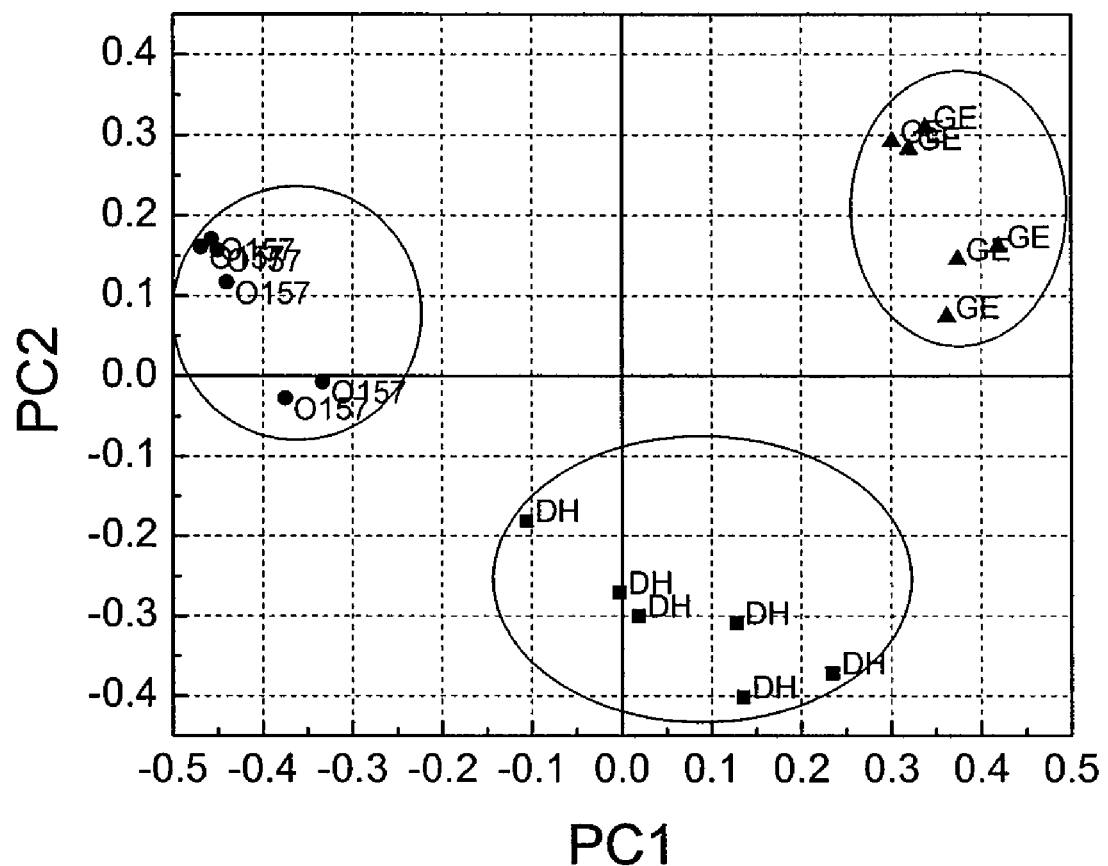
FIG. 22 illustrates PCA scores plot of *E. coli* O157:H7 (O157), *E. coli* DH 5σ (DH) and generic *E. coli* (GE). The PCA model was constructed using the spectral range from 400-1800 $cm^{-1}$.

To be more objective, PCA analysis was carried out for all three sets of SERS spectra for different *E. coli* strains. FIG. 22 shows the PCA score plot using spectral data from *E. coli* O157:H7, generic *E. coli* and *E. coli* DH 5α, in the 400-1800 $cm^{-1}$ range. This score plot shows three different strains of *E. coli* can be separated into three clusters. Based on the PC scores, the cluster for the generic *E. coli* has positive PC1 and PC2 scores, the cluster for *E. coli* O157:H7 has a negative PC1 score. While the cluster for *E. coli* DH has a positive PC1 score (except for one data point), the negative PC2 score separated the cluster from that of generic *E. coli* and *E. coli* O157:H7 having positive PC2 scores.

Viability Specificity

Figure 23:
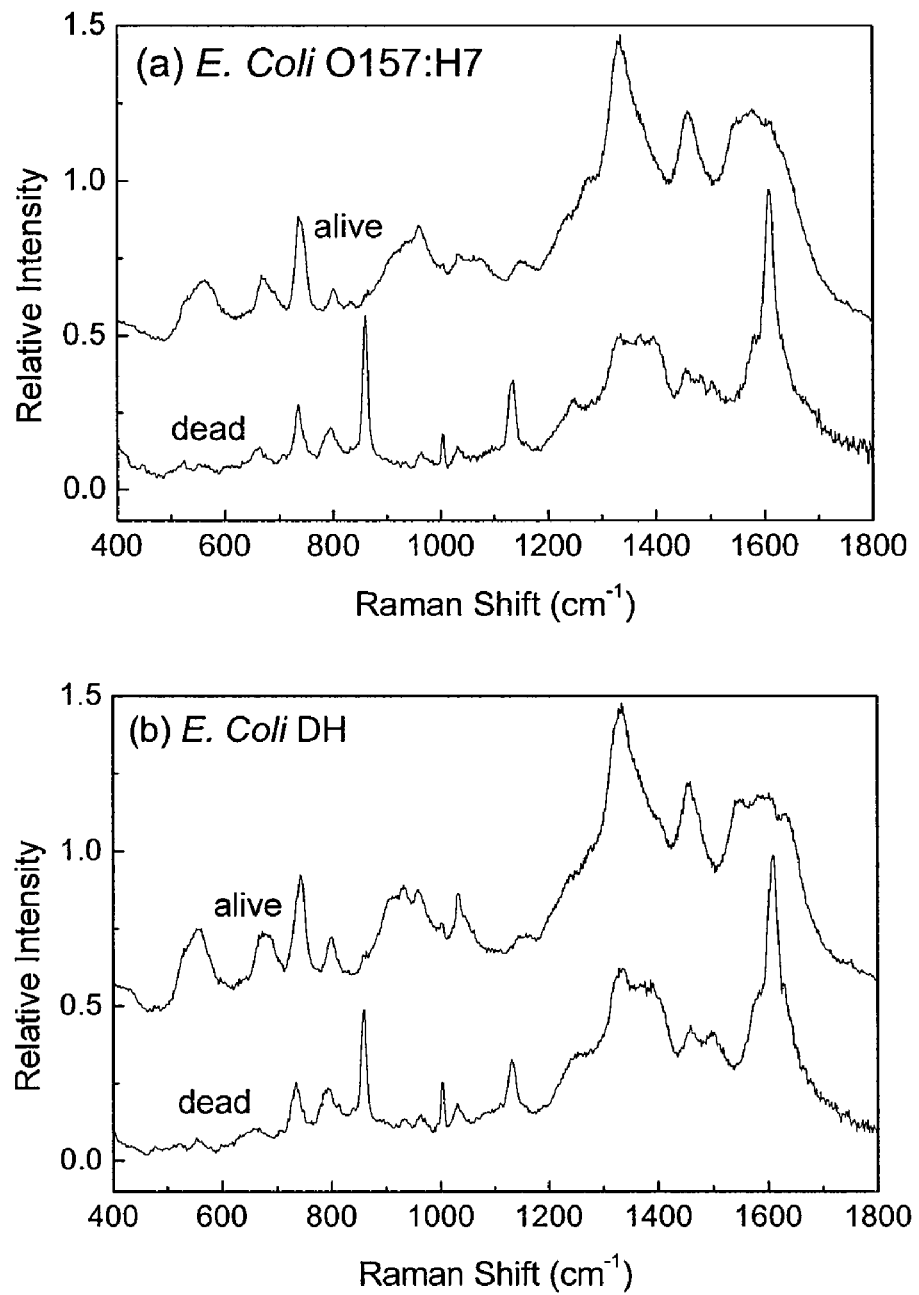
FIG. 23A illustrates SERS spectra of viable *E. coli* O157:H7 and nonviable *E. coli* O157:H7.
FIG. 23B illustrates SERS spectra of viable and nonviable *E. coli* DH 5α. Incident laser powers of 14 mW and collection time of 10 s were used to obtain these spectra. Spectra were offset vertically for display clarity.

Another important aspect for identifying pathogens is the ability to distinguish between viable and nonviable cells. All the spectra we discussed above were obtained from viable cells. FIG. 23A shows spectra of viable and nonviable cells of *E. coli* O157:H7. The nonviable cells were prepared by boiling the bacteria in a hot water bath for 10 min at 100° C. The dead cells show a significantly reduced SERS response at those characteristic bands of ~550 $cm^{-1}$, 735 $cm^{-1}$, 1330 $cm^{-1}$ and 1450 $cm^{-1}$ that are present in the viable cells. Measurements from heat treated *E. coli* DH 5α was also obtained. Significantly reduced SERS responses at major bands from heat treated *E. coli* DH 5α were also observed (FIG. 23B). High temperatures may produce changes in the outer cell layers of bacteria. In Gram negative bacteria, damage to the outer membranes occurs when cells are subjected to a mild heat shock. Heating may significantly denature and cause conformational changes in the outer membrane proteins of Gram negative bacteria. (J. M. DiRienzio, K. Nakamura, and M. Inouye, Annu. Rev. Biochem. 47, 481 (1978), which is incorporated by reference for the corresponding discussion). Heat could also release carbohydrates from cells and separate surface associated carbohydrates from the cell. (J.-H. Ryu, and L. R. Beuchat, J. Appl. Microbiol. 95, 1304 (2003), which is incorporated by reference for the corresponding discussion). Therefore, some variations in the spectra are expected upon heat treatment due to the changes of the structure of the adsorbed molecules or the orientation of the adsorbates. Another possibility is that if SERS bands are due to small molecules produced by the cells, the production of molecules apparently would stop upon cell death. This result is encouraging when considering possible applications of SERS in pathogen detection where the differentiation between viable and nonviable cells is imperative.

SERS Sensitivity

Figure 24:
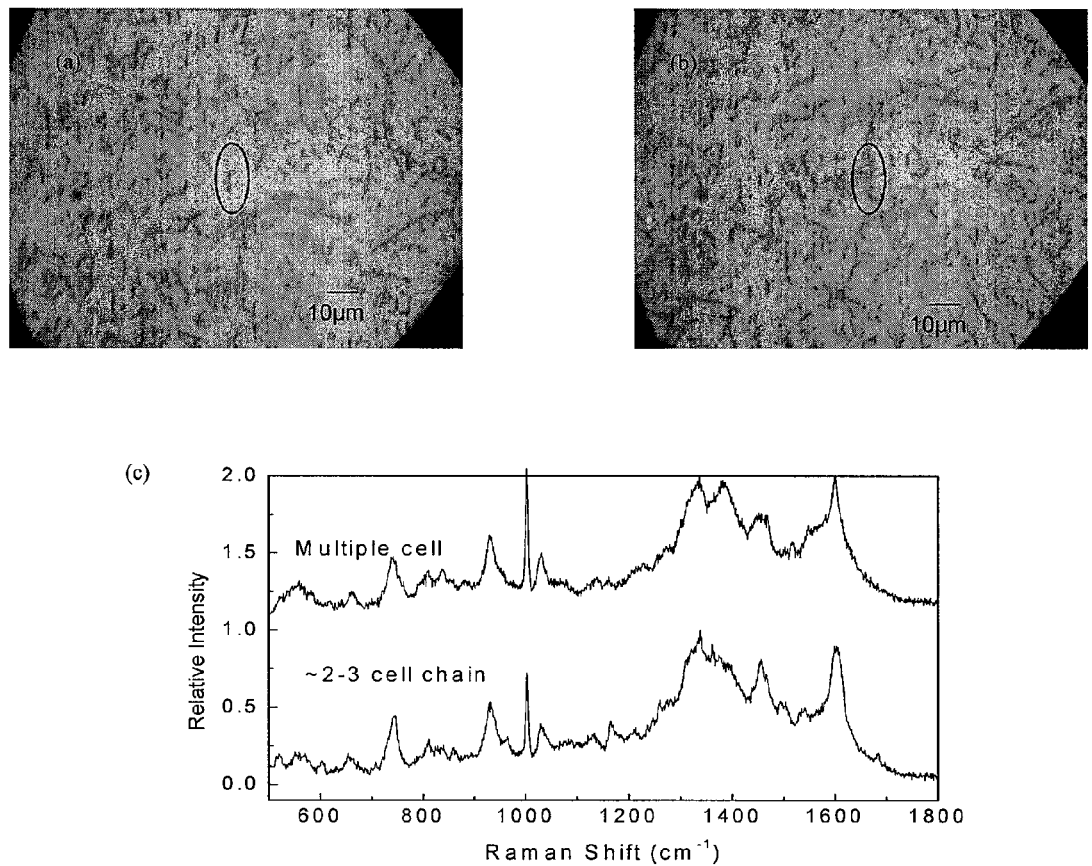
FIGS. 24A through 24C (FIGS. 24A and 24B are digital images) illustrate Raman microscope measurements. Bacteria imaging under 50× microscope objective, single *E. coli* O157:H7 two-three cell chain contributing to the SERS spectrum (FIG. 24A) a multiple cell cluster contributing to the SERS spectrum (FIG. 24B). SERS spectra of single *E. coli* O157:H7 two-three cell chain and a multiple cell cluster are offset vertically for display clarity. Incident laser powers of 12 μW and collection time of 10 s were used to obtain these spectra.

Up to this point, all the spectra were obtained through a HRC-10HT Fiber Raman analyzer system with a 100 µm diameter laser. Typically, a drop of 2 µL of bacteria solution (~$10^8$ CFU/ml) was applied on the substrate forming a spot size of 2 mm in diameter. A calculation indicates that there are roughly 500 cells excited under the 100 µm laser spot. To further explore the sensitivity of SERS technique, SERS spectra of bacteria at the single cell level were observed on our silver nanorod array substrates. A Renishaw Raman microscope, with the ability to probe a much smaller sample area (an approximately 1 µm laser spot), was used to observe the Raman scattering excited by a 785 nm diode laser and a 12 µW laser power. Images of bacterial cells (*E. coli* O157:H7) obtained under a 50× microscope objective are provided in FIG. 24. The area under the focal laser region is highlighted by a circle. FIG. 24A shows an isolate cell chain, consisting of 2-3 cells, where the 1 µm laser beam was focused. A cluster with congested multiple cells is shown in FIG. 24B. The associated Raman spectra, after exposing the area to the 1 µm laser beam for 10 s, are shown in FIG. 24C. The SERS spectrum of the isolated cell chain is quite similar to that of the more congested cells. All the major bands, ~735, 1330, and 1450 cm$^{-1}$, match with what we observed from the lager sample area with a higher number of cells (FIG. 21, estimated ~500 cells excited under the 100 µm laser spot). Most bands correspond to functional groups in the main constituents of a microbial cell, proteins, carbohydrates, lipids, and nucleic acids, which we have described in detail in an earlier section of this report (Species Specificity). Small spectral differences between the spectra collected from larger numbers of cells (i.e., FIG. 21) and those from the isolated cell chain (FIG. 24) may be attributed to the molecular orientation of the components of the bacteria on substrate surface and from the molecular interaction with metal surfaces. These results show the ability to observe Raman signatures of bacteria on a single cell level using the silver nanorod substrate. Non-SERS Raman spectra of a single bacterial cell (*Clostridium beijerinckii*) obtained by a confocal microscopy have been reported. (K. Schuster, I. Reese, E. Urlaub, J. R. Gapes, and B. Lendl, Anal. Chem. 72, 5529 (2000), which is incorporated by reference for the corresponding discussion). However, longer illumination times (3 min) and higher incident laser power (8 mW) was required compared to the considerably low incident power (12 µW) and short illumination time (10 s) employed in our study.

Comparison with Previously Published SERS Spectra of *E. coli*

SERS spectra of *E. coli* obtained with different SERS substrates have been previously reported. There are generally two types of substrates: *E. coli* coated, or suspended with silver colloids (L. Zeiri, B. V. Bronk, Y. Shabtai, J. Czégé, and S. Efrima, Colloids Surfaces A. 208, 357 (2002); L. Zeiri, B. V. Bronk, Y. Shabtai, J. Eichler, and S. Efrima, Appl. Spectrosc. 58, 33 (2004); R. M. Jarvis, A. Brooker, and R. Goodacre, Anal Chem 76, 5198 (2004); A. Sengupta, B. Navpreet, and E. J. Davis, J. Colloid and Interface Sci. 309, 36 (2007), which are incorporated by reference for the corresponding discussion) and *E. coli* deposited on metal surfaces (M. F. Escoriza, J. M. Vanbriesen, S. Sewart, and J. Maier, Appl. Spectrosc. 60, 971 (2006); A. A. Guzelian, J. M. Sylvia, J. A. Janni, S. L. Clauson, and K. M. Spencer, Proc. SPIE. 4577, 182 (2002), which are incorporated by reference for the corresponding discussion) at 514.5 nm, 532 nm, or 785 nm excitation. What is also of note is the different strains of *E. coli* used in different studies. When SERS spectra of the same species obtained from different SERS substrates compared with what we reported here, different patterns of relative intensities and Raman shifted wavenumbers are found. For example, although some of the same bands reported here and by Sengupta, et al. (A. Sengupta, B. Navpreet, and E. J. Davis, J. Colloid and Interface Sci. 309, 36 (2007), which is incorporated by reference for the corresponding discussion), Zeiri, et al. (L. Zeiri, B. V. Bronk, Y. Shabtai, J. Czégé, and S. Efrima, Colloids Surfaces A. 208, 357 (2002); L. Zeiri, B.V. Bronk, Y. Shabtai, J. Eichler, and S. Efrima, Appl. Spectrosc. 58, 33 (2004), which are incorporated by reference for the corresponding discussion), and by Jarvis et al. (R. M. Jarvis, A. Brooker, and R. Goodacre, Anal Chem 76, 5198 (2004), which is incorporated by reference for the corresponding discussion), the most intense band below 800 cm$^{-1}$ is at around 550 cm$^{-1}$ in Jarvis report and also in Zeiri report, around 600 cm$^{-1}$ in Sengupta report and 735 cm$^{-1}$ in our spectra. The differences in SERS signature to those reported by Escoriza, et al. (M. F. Escoriza, J. M. Vanbriesen, S. Sewart, and J. Maier, Appl. Spectrosc. 60, 971 (2006), which is incorporated by reference for the corresponding discussion) and by Guselian, et al. (A. A. Guzelian, J. M. Sylvia, J. A. Janni, S. L. Clauson, and K. M. Spencer, Proc. SPIE. 4577, 182 (2002), which is incorporated by reference for the corresponding discussion), where there are more pronounced bands appear in the 800-1600 cm$^{-1}$ region in our spectra. This indicates to us that the SERS signature of *E. coli* seems to be specific to the SERS active metallic nanostructure.

CONCLUSIONS

A diagnostic method that can identify pathogens rapidly and distinctively with minimum sample preparation has major benefits to prevention of epidemic outbreak and bioterrorism. The SERS method presented here is of practical interest, as it only requires simple sample preparation consisting of washing the cells and drying on a SERS substrate. No chemical reagents are necessary to specifically label target microorganisms; the spectra contain information on all major substances present in bacterial cells. We have demonstrated that good signal-to-noise and reproducible Raman spectra of bacteria when the microorganisms were placed on the silver nanorod array substrate. We evaluated these SERS substrates as potential bioanalytical sensors for bacterial identification. The bacterial SERS fingerprints show clear distinctions between different species and strains; also the ability to distinguish between nonviable and viable cells was presented. The results from PCs plots clearly demonstrate the potential of SERS technique to distinguish different species, to differentiate pure cell sample from mixed cell samples even when there is great similarity among their Raman signatures, and to classify different bacteria strains. The ability to quickly obtain high quality Raman spectra of single bacterial cell would be useful for distinguishing dangerous pathogens in a mixture. The speed, specificity and ease of implementation of SERS technique represents a valuable alternative to current bacterial diagnostic tools and provides the possibility of portable pathogen sensors for on-site food inspection.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and subrange is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure, particularly, any "preferred" embodiments, are merely possible examples of implementations, and are merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

Therefore, at least the following is claimed:

1. A method of detecting at least one bacterium in a sample, comprising:
   exposing a substrate having an array of nanorods on the substrate to the sample, wherein a tilt angle ($\beta$) between an individual nanorod and the substrate surface is about 0° to about 90°, and wherein the sample includes at least one of a first strain of *Escherichia coli* and a second strain of *Escherichia coli*; and
   measuring a surface enhanced Raman spectroscopy (SERS) spectrum, wherein a SERS spectrum of the array of nanorods and the first strain of *Escherichia coli* is detectably different than a SERS spectrum of the array of nanorods and the second strain of *Escherichia coli*.

2. The method of claim 1, wherein the strains of *Escherichia coli* are selected from Generic, O157:H7, or DH 5α.

3. A method of detecting at least one bacterium in a sample, comprising:
   exposing a substrate having an array of nanorods on the substrate to the sample, wherein a tilt angle ($\beta$) between an individual nanorod and the substrate surface is about 0° to about 90°, and wherein the sample includes at least one of a first bacterium and a second bacterium; and
   measuring a surface enhanced Raman spectroscopy (SERS) spectrum, wherein a SERS spectrum of the array of nanorods and the first bacteria is detectably different than a SERS spectrum of the array of nanorods and the second bacteria.

4. The method of claim 3, wherein the first bacterium and the second bacterium are the same type of bacteria but comprise different strains, wherein the first bacterial strain has a first measurable surface-enhanced Raman spectroscopic signature, wherein the second bacterial strain has a second measurable surface-enhanced Raman spectroscopic signature, and wherein the first measurable surface-enhanced spectroscopic signature and the second measurable surface-enhanced Raman spectroscopic signature are distinguishable.

5. The method of claim 4, wherein each of the first bacterium and the second bacterium are selected from *Escherichia*.

6. The method of claim 4, wherein each of the first and the second bacteria are each independently selected from *Escherichia adecarboxylata*, *Escherichia albertii*, *Escherichia blattae*, *Escherichia coli*, *Escherichia fergusonii*, *Escherichia hermannii*, or *Escherichia vulneris*.

7. The method of claim 4, wherein the first bacterium and the second bacterium comprise different strains of *Escherichia coli*.

8. The method of claim 7, wherein the strains of *Escherichia coli* are selected from Generic, O157:H7, or DH 5α.

9. The method of claim 4, further comprising analyzing the measurable surface-enhanced Raman spectroscopic spectrum for each bacterium by the use of an analysis method selected from at least one of Principal Component Analysis (PCA) or K-means Clustering Algorithm analysis.

10. The method of claim 3, wherein the first bacterium and the second bacterium comprise viable or non-viable cells.

11. The method of claim 3, wherein the first bacterium and the second bacterium comprise different gram types.

12. A method of detecting at least one biomolecule in a sample, comprising:
    attaching at least one first biomolecule to an array of nanorods on a substrate, wherein a tilt angle ($\beta$) between an individual nanorod and the substrate surface is about 0° to about 90°;
    exposing the substrate including the first biomolecule to the sample containing at least one of a second biomolecule and a third biomolecule; and
    measuring a surface enhanced Raman spectroscopy (SERS) spectrum, wherein a SERS spectrum of the array of nanorods and the first biomolecule is detectably different than a SERS spectrum of the array of nanorods, the first biomolecule, and the second biomolecule and a SERS spectrum of the array of nanorods, the first biomolecule, and the third biomolecule, and wherein the SERS spectrum of the array of nanorods, the first biomolecule, and the second biomolecule is detectably different than the SERS spectrum of the array of nanorods, the first biomolecule, and the third biomolecule.

13. The method of claim 12, wherein the first biomolecule is selected from: a polynucleotide, a protein, a polypeptide, a glycoprotein, a lipid, a carbohydrate, a fatty acid, a fatty ester, a macromolecular polypeptide complex, or combinations thereof.

14. The method of claim 12, wherein each of the second biomolecule and the third biomolecule are each independently selected from: a polypeptide, a protein, a glycoprotein, a nucleic acid, a eukaryotic cell, a prokaryotic cell, a virus, a bacterium, a protozoa, an apicomplexan, a trematodes, a nematodes, a fungus, a spore, a carbohydrate, a lipid, a vitamin, or combinations thereof.

15. The method of claim 12, wherein each of the second biolmolecule and the third biomolecule are each a bacterium.

16. The method of claim 12, wherein each of the second biomolecule and the third biomolecule are a bacterium selected from *Escherichia*.

17. The method of claim 12, wherein the second biomolecule and the third biomolecule comprise viable or non-viable cells.

18. The method of claim 12, wherein the second biomolecule and the third biomolecule comprise different gram types.

* * * * *